US011446282B2

(12) United States Patent
Oshima et al.

(10) Patent No.: US 11,446,282 B2
(45) Date of Patent: Sep. 20, 2022

(54) METHODS OF TREATING MIXED DYSLIPIDEMIA AND HYPERTRIGLYCERTDEMIA

(71) Applicant: Kowa Company, Ltd., Nagoya (JP)

(72) Inventors: Ryu Oshima, Tokyo (JP); Kazuhito Suehira, Tokyo (JP); Gary Gordon, Morrisville, NC (US)

(73) Assignee: Kowa Company, Ltd., Nagoya (JP)

( * ) Notice: Subject to any disclaimer, the term of this patent is extended or adjusted under 35 U.S.C. 154(b) by 0 days.

(21) Appl. No.: 16/726,857

(22) Filed: Dec. 25, 2019

(65) Prior Publication Data

US 2020/0147051 A1    May 14, 2020

Related U.S. Application Data

(63) Continuation-in-part of application No. 16/227,440, filed on Dec. 20, 2018, now abandoned.

(60) Provisional application No. 62/609,048, filed on Dec. 21, 2017.

(51) Int. Cl.
*A61K 31/423* (2006.01)
*A61P 3/06* (2006.01)

(52) U.S. Cl.
CPC .............. *A61K 31/423* (2013.01); *A61P 3/06* (2018.01)

(58) Field of Classification Search
CPC ................................ A61K 31/423; A61P 3/06
See application file for complete search history.

(56) References Cited

U.S. PATENT DOCUMENTS

| | | | |
|---|---|---|---|
| 7,183,295 B2 | 2/2007 | Yamazaki | |
| 9,931,321 B2 | 4/2018 | Takizawa | |
| 9,968,592 B2 | 5/2018 | Inokuchi | |
| 10,258,609 B2 | 4/2019 | Takizawa | |
| 2018/0028505 A1 | 2/2018 | Oshima | |
| 2018/0028506 A1 | 2/2018 | Oshima | |
| 2019/0167645 A1 | 6/2019 | Takizawa | |

FOREIGN PATENT DOCUMENTS

| | | | |
|---|---|---|---|
| EP | 2141155 A1 | 1/2010 | |
| EP | 3275438 A1 | 1/2018 | |

OTHER PUBLICATIONS

Ishibashi et al; Atherosclerosis, vol. 249, pp. 36-43; Feb. 26, 2016.
Kastelein et al; European Heart Journal; 36 Abstract Supplement, 1048, p. 5983; 2015.
Araki et al; Effects of Pemafibrate, a Novel Selective PPARa Modulator, on Lipid and Glucose Metabolism in Patients With Type 2 Diabetes and Hypertriglyceridemia: A Randomized, Double-Blind, Placebo-Controlled, Phase 3 Trial; Diabetes Care; 2018; 41:538-546.
Araki; Supplementary Data; American Diabetes Association Published online at http://care.diabetesjournals.org/lookup/suppl/doi:10.2337/dc17-1589/-/DC1; 2018.
Blair; Pemafibrate: First Global Approval; Drugs (2017) 77:1805-1810.
Bonds et al; Fenofibrate-associated changes in renal function and relationship to clinical outcomes among individuals with type 2 diabetes: the Action to Control Cardiovascular Risk in Diabetes (ACCORD) experience; Diabetologia. Jun. 2012 ; 55(6): 1641-1650. doi:10.1007/s00125-012-2524-2.
Chapelsky et al; Pharmacokinetics of Rosiglitazone in Patients with Varying Degrees of Renal Insufficiency; Journal of Clinical Pharmacology; 2003; 43: 252-259.
Harper et al; Managing Dyslipidemia in Chronic Kidney Disease; Journal of the American College of Cardiology vol. 51, No. 25, 2008, © 2008 by the American College of Cardiology Foundation ISSN 0735-1097/08/; Published by Elsevier Inc.
Hosford; Dose Adjustment Should be Considered for the Administration of Pemafibrate in Patients with Impaired Hepatic Function; Abstracts/Atherosclerosis Supplements 32 (2018) 1-162.
Hounslow et al; Pemafibrate Has High Bioavailability and is Principally Excreted via the Liver; p. 5.053; Abstracts/Atherosclerosis Supplements 32 (2018) 1-162.
Shibashi et al; Effects of K-877, a novel selective PPARa modulator (SPPARMa), in dyslipidaemic patients: A randomized, double blind, active- and placebo-controlled, phase 2 trial; Atherosclerosis 249 (2016) 36-43; Elsevier.
Liu et al; Early investigational drugs targeting PPAR-a for the treatment of metabolic disease; Expert Opinion on Investigational Drugs, 24:5, 611-621, DOI: 10.1517/13543784.2015.1006359; 2015.
Yamashita; Efficacy and safety of pemafibrate, a novel selective peroxisome proliferator-activated receptor a modulator (SPPARMα): pooled analysis of phase 2 and 3 studies in dyslipidemic patients with or without statin combination; Int. J. Mol. Sci. 2019.
Efficacy and Safety of Pemafibrate, a Novel Selective Peroxisome Proliferator-Activated Receptor a Modulator (SPPARMa): Pooled Analysis of Phase 2 and 3 Studies in Dyslipidemic Patients with or without Statin Combination; Int. J. Mol. Sci. 2019, 20, 5537; 2019.
Yakote et al; Long-Term Efficacy and Safety of Pemafibrate, a Novel Selective Peroxisome Proliferator-Activated Receptor-Modulator (SPPARMa), in Dyslipidemic Patients with Renal Impairment; Int. J. Mol. Sci. 2019, 20, 706; 2019.
Yakote et al; Long-Term Pemafibrate Treatment Was Well Tolerated in Patients with Dyslipidemia Including Those With Kidney Dysfunction; p. 5.049; Abstracts/Atherosclerosis Supplements 32 (2018) 1-162.
Kowa Company, Ltd., EP Application No. 18892061.5, Extended European Search Report, dated Jun. 23, 2021, 11 pp.
Arai, et al., Efficacy and Safety of K-877, a Novel Selective Peroxisome Proliferator-Activated Receptor [alpha] Modulator (SPPARM[alpha]), In Combination With Statin Treatment: Two Randomised Double-Blind, Placebo-Controlled Clinical Trials in Patients With Dyslipidaemia, Atherosclerosis, Elsevier, Amsterdam, NL, vol. 261, Mar. 24, 2017, pp. 144-152.
Takei, et al., Effects of K-877, a Novel Selective PPAR[alpha] Modulator, On Small Intestine Contribute to the Amelioration of Hyperlipidemia in Low-Density Lipoprotein Receptor Knockout Mice, Journal of Pharmacological Sciences, vol. 133, No. 4, Apr. 1, 2017, pp. 214-222.

(Continued)

*Primary Examiner* — Kara R McMillian
(74) *Attorney, Agent, or Firm* — Clark G. Sullivan

(57) ABSTRACT

The present invention relates to pharmacological interventions with pemafibrate for moderate or severe hypertriglyceridemia.

15 Claims, No Drawings

(56) References Cited

OTHER PUBLICATIONS

Ishibashi, et al., Efficacy and Safety of Pemafibrate (K-877), a Selective Peroxisome Proliferator-Activated Receptor [alpha] Modulator, in Patients With Dyslipidemia: Results From a 24-Week, Randomized, Double Blind, Active Controlled, Phase 4 Trial, Journal of Clinical Lipidology, vol. 12, No. 1, Jan. 1, 2018, pp. 173-184.

Fruchart, Charles, Pemafibrate (K-877), a Novel Selective Peroxisome Proliferator-Activated Receptor Alpha Modulator for Management of Atherogenic Dyslipidaemia, Cardiovascular Diabetology, vol. 16., No. 1, Dec. 1, 2017, p. 124.

Arai, Hidenori, Abstract 13118: The Novel Highly Potent and Specific Peroxisome Proliferator-Activated Receptor Alpha Agonist K-877 Improved Liver Enzymes and Lipid Profile Without Adversely Affecting Renal Functions; Integrated Analysis of Phase 2 and Phase 2/3 Double Blind Clinical Trials : Circulation, Circulation 2013, 128, Abstract 13188, Jan. 1, 2013, pp. 1-5.

Ishibashi, et al., Effects of K-877, a Novel Selective PPAR[alpha] Modulator (SPPARM[alpha], In Dyslipidaemic Patients: A Randomized, Double Blind, Active- and Placebo Controlled, Phase 2 Trial, Ahterosclerosis, Elsevier, Amsterdam, NL, vol. 249, Feb. 26, 2016, pp. 36-43.

Trilipix (fenofibrate) FDA-approved Prescribing Information (2018).
Lopid (gemfibrozil) FDA-approved Prescribing Information (2020).
Anderson P, Clinical pharmacokinetics of bezafibrate in patients with impaired renal function. Eur J Clin Pharmacol 1981;21(3):209-14 (abstract).

Gugler R, Clofibrate disposition in renal failure and acute and chronic liver disease. European Journal of Clinical Pharmacology 15, 341-347 (1979) (abstract).

Blair HA, Pemafibrate: First Global Approval. Drugs (2017) 77:1805-1810.

METHODS OF TREATING MIXED DYSLIPIDEMIA AND HYPERTRIGLYCERTDEMIA

FIELD OF THE INVENTION

The present invention relates to pharmacological interventions with pemafibrate for moderate hypertriglyceridemia (serum TG≥200 mg/dL and <500 mg/dL) or severe hypertriglyceridemia (serum TG≥500 mg/dL).

BACKGROUND OF THE INVENTION

A variety of primary disorders of lipoprotein metabolism have been described which may lead to elevated levels of the atherogenic lipoproteins (very low-density lipoprotein (VLDL), remnant particles, low-density lipoprotein (LDL), etc.) or reduced levels of the anti-atherogenic high-density lipoprotein, any or all of which can confer increased risk of coronary artery disease. Of greater concern, elevated levels of triglyceride (TG), in particular TG levels ≥500 mg/dL (5.65 mmol/L), confer an increased risk of acute pancreatitis.[1,2] Acute pancreatitis caused by hypertriglyceridemia (HTG) is associated with increased severity and rates of complications compared to pancreatitis with causes other than HTG.[3,4]

Fibrates improve TG and high-density lipoprotein cholesterol (HDL-C) by activating peroxisome proliferator-activated receptor alpha (PPARα),[5] and are approved in the United States for the treatment of severe HTG. In the United States, fenofibrate, fenofibric acid, and gemfibrozil are available. Fibrates available in Europe are bezafibrate, ciprofibrate, fenofibrate, and gemfibrozil. In Japan, bezafibrate, clinofibrate, clofibrate, and fenofibrate are available.

The United States Adult Treatment Panel III National Cholesterol Education Program (NCEP) guidelines[6] recommend reduction of TG through lifestyle, diet, and pharmacologic methods as the first priority of therapy when serum TG are ≥500 mg/dL. Treatment with omega-3 fatty acids, such as those found in fish oils, has been shown to effectively decrease TG levels up to 30%; however, for individuals with severe HTG, increasing omega-3 fatty acid intake does not adequately manage TG levels.

The European Society for Cardiology and European Atherosclerosis Society consensus guidelines note that patients can develop pancreatitis with TG concentrations between 5 and 10 mmol/L (440 and 880 mg/dL).[8] These guidelines also recommend initiating fibrates to prevent acute pancreatitis.

Most fibrates are contraindicated or require careful administration in patients with renal dysfunction. Furthermore, coadministration of these drugs with statins is contraindicated in patients with severe renal dysfunction. Thus, there are restrictions on the use of existing PPARα agonists.[9,10,11,12,13,14,15,16]

Pemafibrate, whose chemical name is (2R)-2-[3-({1,3-benzoxazol-2-yl[3-(4-methoxyphenoxy)propyl]amino}methyl)phenoxy]butanoic acid, is a PPARα activator like fenofibrate, although it has proven much more potent at affecting lipid metabolism and is more specific for the PPARα receptor than fenofibrate. Thus, pemafibrate is also described as a selective PPARα modulator (SPPARMα). The drug was recently approved for the treatment of hyperlipidemia in Japan and is under development for the treatment of cardiovascular disease world-wide.

Pemafibrate is approximately 2500 times more active than fenofibric acid in terms of the $EC_{50}$ of the PPARα-activating effect. It is more potent than fenofibrate in decreasing TG and increasing HDL-C in apolipoprotein (Apo) A1 transgenic mice. In previous clinical trials, pemafibrate has been administered at doses ranging from 0.1 mg to 1.6 mg per day in healthy adults. Doses up to 0.4 mg per day have been administered in patients with dyslipidemia. Pemafibrate demonstrated dose-dependent decreases in TG in both Japanese and European patients. In study K-877-201, a Phase 2 dose-finding study conducted in Europe, pemafibrate 0.2 mg taken twice daily demonstrated the greatest efficacy with a placebo-adjusted TG reduction of 54.4%. Greater efficacy in TG reduction and HDL-C elevation was observed when pemafibrate was administered twice daily compared to once daily. Treatment with pemafibrate also resulted in changes in the following lipid parameters from baseline to Week 12 with last observation carried forward as determined in the analysis of secondary efficacy endpoints: increases in Apo A1, Apo A2, fibroblast growth factor 21 (FGF21), HDL-C; and decreases in Apo B48, Apo C2, Apo C3, and VLDL-C. Increases in LDL-C, both by beta quantification and calculation with the Friedewald equation, were also observed. Based on analysis of efficacy variables, pemafibrate appeared to have a lowering effect on Apo C3 that led to the conversion of VLDL particles to LDL particles, increasing the fraction of larger LDL particles, and reducing TG levels. Similarly, the reduction of Apo C3 led to increased removal of remnant-like particles and lowering of Apo B48. Overall, no changes were observed in total Apo B levels, indicating that the increase in LDL-C was not associated with an increase in LDL particle number or coronary heart disease (CHD) risk, which was supported by the observed decrease in non-HDL-C, a parameter that more accurately reflects CHD risk than LDL-C. The observed increases in Apo A1 and HDL-C resulted from both increased production of Apo A1 in the liver and increased turnover of TG-rich lipoproteins, both of which were associated with a decreased CHD risk.

Beyond this information, the effect of pemafibrate on the patient with moderate and severe hypertriglyceridemia is unknown. Furthermore, the effect of pemafibrate on the patient with renal impairment along with moderate or severe hypertriglyceridemia, particularly when combined with a statin, is also unknown.

It is therefore an object of the present invention to provide pemafibrate therapies that can treat patients with moderate or severe hypertriglyceridemia along with normal renal function or renal impairment.

SUMMARY OF THE INVENTION

The invention relates to the surprising ability of pemafibrate to reduce plasma triglyceride even in patients with moderate and severe hypertriglyceridemia. Thus, the invention provides a method of treating moderate and severe hypertriglyceridemia in a subject in need thereof, comprising administering to the subject a therapeutically effective amount of pemafibrate or a pharmaceutically acceptable salt thereof. The invention also provides a method of treating moderate or severe hypertriglyceridemia in a subject in need thereof, wherein the patient also is renally impaired, comprising administering to the patient a therapeutically effective amount of pemafibrate or a pharmaceutically acceptable salt thereof.

DETAILED DESCRIPTION OF THE INVENTION

The present invention provides the following:
1) A method of treating moderate or severe hypertriglyceridemia in a subject in need thereof, comprising administering to the patient a therapeutically effective amount of pemafibrate or a pharmaceutically acceptable salt thereof.
2) A method of treating severe hypertriglyceridemia in a subject in need thereof, comprising: (a) identifying a subject having a fasting baseline triglyceride level of about 500 mg/dl (5.65 mmol/L) and over, and (b) administering to the subject a pharmaceutical composition comprising pemafibrate or a pharmaceutically acceptable salt thereof.
3) A method of treating severe hypertriglyceridemia in a subject in need thereof, comprising: (a) identifying a subject having a fasting baseline triglyceride level of about 500 mg/dl (5.65 mmol/L) to about 2000 mg/dl (22.6 mmol/L), and (b) administering to the subject a pharmaceutical composition comprising pemafibrate or a pharmaceutically acceptable salt thereof.
4) The method according to any one of 1) to 3), wherein the therapeutically effective amount of pemafibrate or pharmaceutically acceptable salt thereof is from 0.2 to 1.0 mg, administered orally per day.
5) The method according to any one of 1) to 3), wherein the therapeutically effective amount of pemafibrate or pharmaceutically acceptable salt thereof is 0.4 mg, administered orally per day.
6) The method according to 5), wherein the therapeutically effective amount of pemafibrate or pharmaceutically acceptable salt thereof is administered twice daily.
7) The method according to any one of 1) to 3), wherein the therapeutically effective amount of pemafibrate or a pharmaceutically acceptable salt thereof is 0.2 mg, administered orally per day.
8) The method according to 7), wherein the therapeutically effective amount of pemafibrate or pharmaceutically acceptable salt thereof is administered twice daily.
9) The method according to any one of 1) to 3), wherein the patient has normal renal function.
10) The method according to any one of 1) to 3), wherein the patient has mild or moderate renal impairment.
11) The method according to any one of 1) to 8), wherein the patient has severe renal impairment.
12) The method of any one of 1) to 11), wherein the patient is on high intensity statin therapy and aged ≥21 years with clinical ASCVD selected from a history of acute coronary syndrome or myocardial infarction, stable or unstable angina, coronary revascularization, stroke, transient ischemic attack [TIA] of atherosclerotic origin, or peripheral arterial disease or revascularization.
13) The method of any one of 1) to 11), wherein the patient is on high intensity statin therapy and aged ≥21 years with a history of LDL-C≥190 mg/dL, which is not due to secondary modifiable causes.
14) The method of any one of 1) to 11), wherein the patient is on moderate or high intensity statin therapy and aged 40 to 75 years, inclusive, without clinical ASCVD but with type-2 diabetes and a history of LDL-C of 70 to 189 mg/dL, inclusive.
15) The method of any one of 1) to 11), wherein the patient is on moderate or high intensity statin therapy and aged 40 to 75 years, inclusive, without clinical ASCVD or diabetes, with a history of LDL-C of 70 to 189 mg/dL, inclusive, with estimated 10-year risk for ASCVD of ≥7.5% by the Pooled Cohort Equation.
16) The method of any one of 1) to 15), wherein the subject has one or a combination of low HDL-C levels, elevated LDL-C levels, elevated non-HDL-C levels, or elevated Total Cholesterol levels.
17) The method of any one of 1) to 16), wherein said subject is an adult and not on statin therapy, comprising administering 0.2 mg of pemafibrate or a pharmaceutically acceptable salt thereof twice daily to said subject, further comprising administering 0.2 mg of pemafibrate or a pharmaceutically acceptable salt thereof to a second adult subject on moderate or high intensity statin therapy with moderate or severe hypertriglyceridemia.
18) The method of 17), wherein said second adult subject is on high intensity statin therapy.
19) The method of any one of 1) to 17) wherein said subject is an adult and not renally impaired, comprising administering 0.2 mg of pemafibrate or a pharmaceutically acceptable salt thereof twice daily to said subject, further comprising administering 0.2 mg of pemafibrate or a pharmaceutically acceptable salt thereof to a second adult subject who is renally impaired with moderate or severe hypertriglyceridemia.
20) The method of 19), wherein said second subject has mild to moderate renal impairment.
21) The method of any one of 1) to 20), wherein the subject has a fasting baseline triglyceride level of greater than 750 mg/dl (8.475 mmol/L).
22) The method of any one of 1) to 20), wherein the subject has a fasting baseline triglyceride level of greater than 1000 mg/dl (11.3 mmol/L).
23) The method of any one of 1) to 20), wherein the subject has a fasting baseline triglyceride level of greater than 1500 mg/dl (16.95 mmol/L).
24) A method of treating dyslipidemia in a renally impaired adult patient and a non-renally impaired adult patient comprising administering to both patients 0.2 mg of pemafibrate or a pharmaceutically acceptable salt thereof twice daily.
25) The method of 24) wherein the renally impaired patient is mildly to moderately renally impaired.
26) The method of 24) wherein the renally impaired patient is severely renally impaired.
27) The method of any one of 1) to 26) wherein the subject or renally impaired patient has an HDL-C concentration of less than 40 mg/dL.
28) The method of any one of 1) to 26) wherein the subject or renally impaired patient is on moderate or high intensity statin therapy.
29) The method of any one of 1) to 26) wherein the subject has an LDL-C concentration less than 70 mg/dL.
30) The method of any one of 1) to 26) wherein the subject or renally impaired patient has an HDL-C concentration of less than 40 mg/dL and is on moderate to high intensity statin therapy.
31) The method of any one of 1) to 26) wherein the subject or renally impaired patient has an HDL-C concentration of less than 40 mg/dL and has an LDL-C concentration less than 70 mg/dL.
32) The method of 1) wherein the subject or renally impaired patient has an HDL-C concentration of less than 40 mg/dL and is on moderate to high intensity statin therapy and has a triglyceride concentration of from 200 to 500 mg/dL.
33) The method of 1) wherein the subject or renally impaired patient has an HDL-C concentration of less than 40 mg/dL and has an LDL-C concentration less than 70 mg/dL and has a triglyceride concentration of from 200 to 500 mg/dL.
34) The method of any one of 1) to 33) wherein the method prevents a cardiovascular event selected from nonfatal myocardial infarction, nonfatal ischemic stroke, hospitalization for unstable angina requiring unplanned coronary revascularization, cardiovascular death, and combinations thereof.
35) A method of treating atherogenic dyslipidemia in a renally impaired dyslipidemic patient having an estimated glomerular filtration rate (eGFR) of less than 60 mL/min/1.73 m$^2$ comprising administering to the patient a therapeutically effective amount of pemafibrate or a pharmaceutically acceptable salt thereof in combination with moderate to high intensity statin therapy.
36) A method of simultaneously reducing small to very small LDL-C particles and increasing small to very small HDL-C particle sizes in a renally impaired dyslipidemic patient having an estimated glomerular filtration rate (eGFR) of less than 60 mL/min/1.73 m$^2$ comprising administering to the patient a therapeutically effective amount of pemafibrate or a pharmaceutically acceptable salt thereof in combination with moderate to high intensity statin therapy.
37) A method of lowering LDL-C in a renally impaired dyslipidemic patient having an estimated glomerular filtration rate (eGFR) of less than 30 mL/min/1.73 m$^2$ comprising administering to the patient a therapeutically effective amount of pemafibrate or a pharmaceutically acceptable salt thereof in combination with moderate to high intensity statin therapy.
38) The method of 35 or 36, wherein the patient has an eGFR of less than 45 mL/min/1.73 m$^2$.
39) The method of 35 or 36, wherein the patient has an eGFR of less than 30 mL/min/1.73 m$^2$.
40) The method of any of 35-39, wherein the patient has end stage renal disease.
41) The method of any of 35-40, wherein the patient has chronic kidney disease.
42) The method of any of 35-41, wherein the therapeutically effective amount of pemafibrate comprises about 0.4 mg per day.
43) The method of any of 35-42, wherein said patient is characterized by increased TG-rich lipoproteins and decreased HDL-C levels.
44) The method of any of 35-43, wherein said patient has a TG concentration greater than 150 ng/mL.

As used in the specification and claims, the singular forms "a," "an," and "the" include plural references unless the context clearly dictates otherwise. For example, the term "a pharmaceutical excipient" refers to one or more pharmaceutical excipients for use in the presently disclosed formulations and methods.

The use of numerical values in the various quantitative values specified in this application, unless expressly indicated otherwise, are stated as approximations as though the minimum and maximum values within the stated ranges were both preceded by the word "about". Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

As used herein, "therapeutically effective amount" refers to an amount sufficient to elicit the desired biological response in a patient. The therapeutically effective amount or dose depends on the age, sex and weight of the patient, and the current medical condition of the patient. The skilled artisan can determine appropriate amount or dose depending on the above factors based on his or her knowledge and the teachings contained herein.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use. "Pharmaceutically acceptable salts" means salts that are pharmaceutically acceptable, as defined above, and which possess the desired pharmacological activity.

The terms "treating" and "treatment," when used herein, refer to the medical management of a patient with the intent to cure, ameliorate, stabilize, or prevent a disease, pathological condition, or disorder (collectively "disorder"). These terms include active treatment, that is, treatment directed specifically toward the improvement of a disorder, and also include causal treatment, that is, treatment directed toward removal of the cause of the associated disorder. In addition, this term includes palliative treatment, that is, treatment designed for the relief of symptoms rather than the curing of the disorder; preventative treatment, that is, treatment directed to minimizing or partially or completely inhibiting or delaying the development of the disorder; and supportive treatment, that is, treatment employed to supplement another specific therapy directed toward the improvement of the disorder.

All analyte measurements recited herein, when used to define a patient described herein, are measured at the beginning of pemafibrate treatment.

Unless stated herein to the contrary, all analyte measurements are taken in the fasting state, and are based on the concentration of the analyte in plasma or serum. The fasting state means that the patient has not eaten anything in from 8 to 12 hours, except for water. Standard methods of measuring analytes can be found in Lab Protocols for NHANES 2003-2004 data published by the United States Centers for Disease Control.

Unless stated herein to the contrary, all methods described herein are performed in all ages, preferably greater than 18 years.

As used herein, the term "significantly" refers to a level of statistical significance. The level of statistical significant can be, for example, of at least $p<0.05$, of at least $p<0.01$, of at least $p<0.005$, or of at least $p<0.001$.

As used herein, the term "normal renal function" refers to a situation in which the renal function of the patient of this invention is normal. In general, an estimated glomerular filtration rate (eGFR) of 90 mL/min/1.73 m$^2$ or more (eGFR≥90) qualifies as normal renal function.

As used herein, the term "mild renal impairment" refers to a situation in which the renal function of the patient of this invention is mildly impaired. In general, an eGFR less than 90 mL/min/1.73 m$^2$ and greater than or equal to 60 mL/min/1.73 m$^2$ (60≤eGFR≤90) qualifies as mild renal impairment.

As used herein, the term "moderate renal impairment" refers to a situation in which the renal function of the patient of this invention is moderately impaired. In general, an eGFR less than 60 mL/min/1.73 m² and greater than or equal to 30 mL/min/1.73 m² (30≤eGFR≤60) qualifies as moderate renal impairment.

As used herein, the term "mild or moderate renal impairment" refers to a situation in which the renal function of the patient of this invention is mildly or moderately impaired. In general, an eGFR less than 90 mL/min/1.73 m² and greater than or equal to 30 mL/min/1.73 m² (30≤eGFR≤90) qualifies as mild or moderate renal impairment.

As used herein, the term "severe renal impairment" refers to a situation in which the renal function of the patient of this invention is severely impaired. In general, an eGFR less than 30 mL/min/1.73 m² (eGFR<30) qualifies as severe renal impairment.

ASCVD when used herein refers to atherosclerotic cardiovascular disease.

The "Pooled Cohort Equation" is reported at Preiss D, Kristensen S L, *The new pooled cohort equations risk calculator*. CAN J CARDIOL. 2015 May; 31(5):613-9.

Statins, also known as HMG-CoA reductase inhibitors, include atorvastatin, simvastatin, fluvastatin, pitavastatin, rosuvastatin, pravastatin, and lovastatin and their pharmaceutically acceptable salts. Statins are generally classified as high, moderate or low intensity, based on the degree of LDL-C reduction they have demonstrated in controlled clinical trials, as summarized in the following table derived from *ACC/AHA Release Updated Guideline on the Treatment of Blood Cholesterol to Reduce ASCVD Risk*, AMERICAN FAMILY PHYSICIAN, Volume 90, Number 4 (Aug. 15, 2014):

discloses lipid cut-points for evaluating cardiovascular risk. Under these cut-points, a person having an LDL-C concentration greater than 100 mg/dL (2.59 mmol/L) or even 70 mg/dL (1.81 mmol/L) is at risk for a cardiovascular event. A person having a total cholesterol concentration greater than 200 mg/dL (5.18 mmol/L) is at risk for a cardiovascular event. A person having an HDL-C concentration less than 40 mg/dL (1.0 mmol/L) for men and less than 50 mg/dL (1.3 mmol/L) for women is at risk for a cardiovascular event. A person having a fasting triglyceride concentration greater than 200 mg/dL (2.27 mmol/dL) or even 150 mg/dL (1.70 mmol/L) is at risk for cardiovascular events. A person having a non-HDL-C concentration greater than 130 mg/dL (3.37 mmol/L) is also at risk for a cardiovascular event.

While the methods of the present invention are particularly useful in the treatment of elevated triglycerides, they also are useful for the treatment of patients with one or a combination of low HDL-C levels, elevated LDL-C levels, elevated non-HDL-C levels, or elevated Total Cholesterol levels. Thus, the methods are also useful for the treatment of patients with:

low HDL-C
elevated LDL-C
elevated non-HDL-C
elevated Total Cholesterol
low HDL-C and elevated LDL-C
low HDL-C and elevated non-HDL-C
low HDL-C and elevated Total Cholesterol
low HDL-C and elevated LDL-C and elevated non-HDL-C

| High intensity | Moderate intensity | Low intensity |
| --- | --- | --- |
| Daily dosage lowers LDL-C by approximately ≥ 50% on average | Daily dosage lowers LDL-C by approximately 30% to 50% on average | Daily dosage lowers LDL-C by approximately < 30% on average |
| Atorvastatin, 40 to 80 mg | Atorvastatin, 10 (*20*) mg | *Simvastatin, 10 mg* |
| Rosuvastatin, 20 (40) mg | Rosuvastatin, (5) 10 mg | Pravastatin, 10 to 20 mg |
| | Simvastatin, 20 to 40 mg | Lovastatin, 20 mg |
| | Pravastatin, 40 (*80*) mg | *Fluvastatin, 20 to 40 mg* |
| | Lovastatin, 40 mg | *Pitavastatin, 1 mg* |
| | *Fluvastatin XL, 80 mg* | |
| | Fluvastatin, 40 mg twice daily | |
| | *Pitavastatin, 2 to 4 mg* | |

NOTE:
Specific statins and dosages noted in bold were evaluated in RCTs included in critical question 1, critical question 2, and the Cholesterol Treatment Trialists 2010 meta-analysis included in critical question 3 (see full guideline for details). All of these RCTs demonstrated a reduction in major cardiovascular events. Statins and dosages listed in italics are approved by the U.S. Food and Drug Administration but were not tested in the RCTs reviewed. RCT = randomized clinical trial.

When the term "moderate to high intensity statin therapy" is employed, the following group of statin therapies is preferably administered, and can be substituted for the term "moderate to high intensity statin therapy": atorvastatin ≥40 mg/day (based on the weight of the free base), rosuvastatin ≥20 mg/day (based on the weight of the calcium salt), and simvastatin ≥40 mg/day (based on the weight of the free base), or pitavastatin ≥4 mg/day. The term "non-moderate to high intensity statin therapy" refers to any statin therapy other than atorvastatin ≥40 mg/day (based on the weight of the free base), rosuvastatin ≥20 mg/day (based on the weight of the calcium salt), and simvastatin ≥40 mg/day (based on the weight of the free base), or pitavastatin ≥4 mg/day.

As used herein, a patient tested for a biomarker that is "elevated" or "low" means that the patient is at risk for an adverse cardiovascular event. The Third Report of the National Cholesterol Education Program ("NCEP") Expert Panel on Detection, Evaluation, and Treatment of High Blood Cholesterol in Adults (Adult Treatment Panel III)

low HDL-C and elevated LDL-C and elevated Total Cholesterol
low HDL-C and elevated non-HDL-C and elevated Total Cholesterol
low HDL-C and elevated LDL-C and elevated non-HDL-C and elevated Total Cholesterol
elevated LDL-C and elevated non-HDL-C
elevated LDL-C and elevated Total Cholesterol
elevated LDL-C and elevated non-HDL-C and elevated Total Cholesterol
elevated non-HDL-C and elevated Total Cholesterol
increased TG-rich lipoproteins and decreased HDL-C levels.
a TG concentration greater than 150 ng/mL.

Total pemafibrate daily doses ranging from 0.1 mg to 0.4 mg, administered daily or divided twice daily, have demonstrated an acceptable safety profile. Because the urinary excretion of pemafibrate is low, as shown by nonclinical and clinical studies, it is expected that pemafibrate can be used safely even in patients with renal impairment. In addition, because the drug has minimal inhibitory effects on major drug metabolizing enzymes in the liver, it is unlikely to cause drug-drug interactions; however, drugs which are strong organic anion-transporting polypeptide (OATP) inhibitors (e.g., cyclosporine and rifampin) do interact with pemafibrate. Therefore, pemafibrate is expected to exhibit not only a potent lipid metabolism-improving effect but also to serve as a drug with a broad therapeutic range with fewer restrictions in patients with renal dysfunction or with concomitant drugs than existing PPARα agonists.

Data from study K-877-12 in Japanese patients with renal impairment found no meaningful differences in pemafibrate pharmacokinetics (PK), even in patients with severe renal impairment, suggesting adjustment of dosing for renal impairment will not be necessary with pemafibrate to ensure patient safety.

In a first embodiment, the invention provides a method of treating moderate or severe hypertriglyceridemia in a subject in need thereof, comprising administering to the patient a therapeutically effective amount of pemafibrate or a pharmaceutically acceptable salt thereof.

According to this embodiment, moderate or severe hypertriglyceridemia can be treated.

In a preferred first embodiment, the therapeutically effective amount of pemafibrate or pharmaceutically acceptable salt thereof is from 0.2 to 1.0 mg, administered orally per day.

In a preferred first embodiment, the therapeutically effective amount of pemafibrate or pharmaceutically acceptable salt thereof is about 0.4 mg, administered orally per day.

In a preferred first embodiment, the therapeutically effective amount of pemafibrate or pharmaceutically acceptable salt thereof is administered twice daily.

In a preferred first embodiment, the patient has normal renal function.

In a preferred first embodiment, the patient has mild or moderate renal impairment.

In another preferred first embodiment the subject has an HDL-C concentration of less than 40 mg/dL.

In another preferred first embodiment the subject is on moderate or high intensity statin therapy.

In another preferred first embodiment the subject has an LDL-C concentration less than 70 mg/dL.

In another preferred first embodiment the subject has an HDL-C concentration of less than 40 mg/dL and is on moderate to high intensity statin therapy.

In another preferred first embodiment the subject or renally impaired patient has an HDL-C concentration of less than 40 mg/dL and has an LDL-C concentration less than 70 mg/dL.

In another preferred first embodiment the method prevents a cardiovascular event selected from nonfatal myocardial infarction, nonfatal ischemic stroke, hospitalization for unstable angina requiring unplanned coronary revascularization, cardiovascular death, and combinations thereof.

In another preferred first embodiment the subject has an HDL-C concentration of less than 40 mg/dL and is on moderate to high intensity statin therapy and has a triglyceride concentration of from 200 to 500 mg/dL.

In another preferred first embodiment the subject has an HDL-C concentration of less than 40 mg/dL and has an LDL-C concentration less than 70 mg/dL and has a triglyceride concentration of from 200 to 500 mg/dL.

In a second embodiment, the invention provides a method of treating severe hypertriglyceridemia in a subject in need thereof, comprising: (a) identifying a subject having a fasting baseline triglyceride level of about 500 mg/dl (5.65 mmol/L) and over, and (b) administering to the subject a pharmaceutical composition comprising pemafibrate or a pharmaceutically acceptable salt thereof.

In a preferred second embodiment, the therapeutically effective amount of pemafibrate or pharmaceutically acceptable salt thereof is from 0.2 to 1.0 mg, administered orally per day.

In a preferred second embodiment, the therapeutically effective amount of pemafibrate or pharmaceutically acceptable salt thereof is about 0.4 mg, administered orally per day.

In a preferred second embodiment, the therapeutically effective amount of pemafibrate or pharmaceutically acceptable salt thereof is administered twice daily.

In a preferred second embodiment, the patient has normal renal function.

In a preferred second embodiment, the patient has mild or moderate renal impairment.

In another preferred first embodiment the subject has an HDL-C concentration of less than 40 mg/dL.

In another preferred second embodiment the subject is on moderate or high intensity statin therapy.

In another preferred second embodiment the subject has an LDL-C concentration less than 70 mg/dL.

In another preferred second embodiment the subject has an HDL-C concentration of less than 40 mg/dL and is on moderate to high intensity statin therapy.

In another preferred second embodiment the subject or renally impaired patient has an HDL-C concentration of less than 40 mg/dL and has an LDL-C concentration less than 70 mg/dL.

In another preferred second embodiment the method prevents a cardiovascular event selected from nonfatal myocardial infarction, nonfatal ischemic stroke, hospitalization for unstable angina requiring unplanned coronary revascularization, cardiovascular death, and combinations thereof.

In a third embodiment, the invention provides a method of treating severe hypertriglyceridemia in a subject in need thereof, comprising: (a) identifying a subject having a fasting baseline triglyceride level of about 500 mg/dl (5.65 mmol/L) to about 2000 mg/dl (22.6 mmol/L), and (b) administering to the subject a pharmaceutical composition comprising pemafibrate or a pharmaceutically acceptable salt thereof.

In a preferred third embodiment, the therapeutically effective amount of pemafibrate or pharmaceutically acceptable salt thereof is from 0.2 to 1.0 mg, administered orally per day.

In a preferred third embodiment, the therapeutically effective amount of pemafibrate or pharmaceutically acceptable salt thereof is about 0.4 mg, administered orally per day.

In a preferred third embodiment, the therapeutically effective amount of pemafibrate or pharmaceutically acceptable salt thereof is administered twice daily.

In a preferred third embodiment, the patient has normal renal function.

In a preferred third embodiment, the patient has mild or moderate renal impairment.

In another preferred third embodiment the subject has an HDL-C concentration of less than 40 mg/dL.

In another preferred third embodiment the subject is on moderate or high intensity statin therapy.

In another preferred third embodiment the subject has an LDL-C concentration less than 70 mg/dL.

In another preferred third embodiment the subject has an HDL-C concentration of less than 40 mg/dL and is on moderate to high intensity statin therapy.

In another preferred third embodiment the subject or renally impaired patient has an HDL-C concentration of less than 40 mg/dL and has an LDL-C concentration less than 70 mg/dL.

In another preferred third embodiment the method prevents a cardiovascular event selected from nonfatal myocardial infarction, nonfatal ischemic stroke, hospitalization for unstable angina requiring unplanned coronary revascularization, cardiovascular death, and combinations thereof.

The dosing of the pemafibrate is preferably defined based on route of administration, dose, and length of treatment. The preferred route of administration is oral. Pemafibrate can be administered to a patient in the fed or fasting state.

The therapeutically effective amount of pemafibrate can be defined as a range of suitable doses on a daily basis. Thus, in one embodiment the therapeutically effective amount is from 0.1 to 1.0 mg of pemafibrate or a pharmaceutically acceptable salt thereof, administered orally per day.

In another embodiment the therapeutically effective amount is from 0.2 to 0.8 mg of pemafibrate or a pharmaceutically acceptable salt thereof, administered orally per day. In still another embodiment the therapeutically effective amount is about 0.4 mg of pemafibrate or a pharmaceutically acceptable salt thereof, administered orally per day. Unless otherwise stated, these doses are based on the weight of the free base of pemafibrate.

The dose of pemafibrate can be administered as one dose per day or in two, three or four evenly divided doses per day.

In some embodiments, pemafibrate can be administered for a therapeutically effective period of time. The therapeutically effective period of time refers to the period of time necessary to treat moderate or severe hypertriglyceridemia, and varies depending on the conditions of a patient being treated and other factors such as the patient's age. The therapeutically effective period of time generally equates to three or more months of treatment, six or more months, one or more years, two or more years, three or more years, or four or more years.

Advantages of the invention are set forth in part in the foregoing description, and in part will be obvious from the description, or may be learned by practice of the invention. The advantages of the invention will be realized and attained by means of the elements and combinations particularly pointed out in the appended claims. It is to be understood that both the description herein is exemplary and explanatory only and not restrictive of the invention, as claimed.

Other embodiments of the invention may be apparent to those skilled in the art from consideration of the specification and practice of the invention disclosed herein. It is intended that the specification and examples be considered as exemplary only, with a true scope and spirit of the invention being indicated by the following claims.

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention.

Example 1 Treatment of Severe Hypertriglyceridemia with Pemafibrate

Title of Study:
A Phase 3, Multi-Center, Placebo-Controlled, Randomized, Double-Blind, 12-Week Study With a 40-Week, Active-Controlled, Double-Blind Extension to Evaluate the Efficacy and Safety of Pemafibrate in Adult Patients With Fasting Triglyceride Levels ≥500 mg/dL and <2000 mg/dL and Normal Renal Function.

Study Design:
Study K-877-301 is a Phase 3, multi-center, randomized, double-blind study to confirm the efficacy and safety of pemafibrate 0.2 mg twice daily compared to matching placebo (in the 12-week Efficacy Period) and an active comparator, fenofibrate (in the 40-week Extension Period), in patients with fasting triglyceride (TG) levels 2500 mg/dL (5.65 mmol/L) and <2000 mg/dL (22.60 mmol/L) and normal renal function.

Eligible patients enter a 4- to 6-week lifestyle stabilization period (4-week stabilization for patients not requiring washout and 6-week washout and stabilization for patients on lipid-altering therapy other than statins, ezetimibe, or proprotein convertase subtilisin/kexin type 9 [PCSK9] inhibitors). The stabilization period is followed by a 2-week TG qualifying period (Visits 2 [Week −2] and 3 [Week −1]), and patient eligibility is assessed based on the mean TG value from these 2 visits. If the patient's mean TG level during the TG qualifying period is ≥450 mg/dL (5.09 mmol/L) and <500 mg/dL (5.65 mmol/L), an additional TG measurement can be taken 1 week later at Visit 3.1. The mean of all 3 TG measurements is used to determine eligibility for the study. After confirmation of qualifying fasting TG values, eligible patients enter a 12-week, randomized, double-blind Efficacy Period. At Visit 4 (Day 1), patients are randomly assigned in a 2:1 ratio to pemafibrate 0.2 mg twice daily or identical matching placebo tablets twice daily. During the 12-week Efficacy Period, patients return to the site at Visit 5 (Week 4), Visit 6 (Week 8), and Visit 7 (Week 12) for efficacy and safety evaluations.

Patients who successfully complete the 12-week Efficacy Period are eligible to continue in a 40-week, double-blind, active-controlled Extension Period after completing the Visit 7 (Week 12) procedures. Patients randomized to receive pemafibrate 0.2 mg twice daily in the 12-week Efficacy Period continue to receive pemafibrate 0.2 mg twice daily, as well as placebo matching fenofibrate 145 mg once daily, in the 40-week Extension Period. Patients randomized to receive placebo matching pemafibrate 0.2 mg twice daily in the 12-week Efficacy Period receive fenofibrate 145 mg once daily and placebo matching pemafibrate 0.2 mg twice daily in the 40-week Extension Period.

From Visit 7 (Week 12), patients not on statins, ezetimibe, or PCSK9 inhibitors may initiate therapy, and patients receiving statins, ezetimibe, or PCSK9 inhibitors may alter their dose, as indicated by guidelines or local standard of care.

After Visit 8 (Week 16), patients are to return to the site every 12 weeks until the last visit (Visit 11 [Week 52]).

Primary Objective:
The primary objective of the study is to demonstrate the efficacy of pemafibrate 0.2 mg twice daily compared to placebo from baseline to Week 12 in lowering fasting TG levels in patients with fasting TG levels ≥500 mg/dL (5.65 mmol/L) and <2000 mg/dL (22.60 mmol/L).

Secondary Objectives:

The secondary objectives of the study are the following:

To evaluate the efficacy of pemafibrate 0.2 mg twice daily from baseline to Week 52 in lowering fasting TG levels in patients with fasting TG levels ≥500 mg/dL (5.65 mmol/L) and <2000 mg/dL (22.60 mmol/L);

To evaluate the efficacy of pemafibrate 0.2 mg twice daily from baseline to Week 12 and Week 52 in altering lipid parameters in patients with fasting TG levels ≥500 mg/dL (5.65 mmol/L) and <2000 mg/dL (22.60 mmol/L);

To evaluate the safety and tolerability of pemafibrate 0.2 mg twice daily in patients with fasting TG levels ≥500 mg/dL (5.65 mmol/L) and <2000 mg/dL (22.60 mmol/L); and To determine the plasma concentrations of pemafibrate for the purpose of use in population pharmacokinetic (PK) analysis and PK/pharmacodynamic (PD) analysis.

Exploratory Objective:

The exploratory objective of the study is to evaluate signs of potential efficacy of pemafibrate 0.2 mg twice daily in treating non-alcoholic fatty liver disease in patients with fasting TG levels ≥500 mg/dL (5.65 mmol/L) and <2000 mg/dL (22.60 mmol/L)

Patient Population:

The study population consist of male and female patients 218 years of age with fasting TG levels ≥500 mg/dL (5.65 mmol/L) and <2000 mg/dL (22.60 mmol/L) after washout from background lipid-altering therapy other than statins, ezetimibe, or PCSK9 inhibitors and with normal renal function. Stable therapy with statins, ezetimibe, or PCSK9 inhibitors is allowed. The 40-week, active-controlled Extension Period population consists of patients completing the 12-week placebo-controlled Efficacy Period. Patients in the 40-week, active-controlled Extension Period are allowed to continue in the study even if the background lipid-altering therapy with statins, ezetimibe, or PCSK9 inhibitors requires adjustment.

Number of Patients:

Approximately 630 patients (420 patients receiving pemafibrate; 210 patients receiving placebo/fenofibrate)

Dose Levels:

12-Week Efficacy Period

Pemafibrate: 0.2 mg twice daily

Placebo: twice daily

40-Week Extension Period

Pemafibrate: 0.2 mg twice daily/fenofibrate matching placebo: once daily

Fenofibrate: 145 mg once daily/Pemafibrate matching placebo: twice daily

Route of Administration:

Oral

Duration of Treatment:

This study consists of a 12-week, double-blind, placebo-controlled Efficacy Period, followed by a 40-week, double-blind, active-controlled Extension Period, for a total of 52 weeks on study drug.

Criteria for Evaluation:

Efficacy:

The primary efficacy endpoint is the percent change in fasting TG from baseline to Week 12. Baseline for TG is defined as the mean of Visit 4 (Day 1) and the preceding TG qualifying visit (either Visit 3 [Week −1] or Visit 3.1, if required) measurements.

The secondary efficacy endpoints for the 12-week Efficacy Period include the following:

Percent change from baseline to Week 12 in remnant cholesterol (calculated as total cholesterol [TC]-low-density lipoprotein C [LDL-C]-high-density lipoprotein C [HDL-C]), HDL-C, apolipoprotein (Apo) A1, and non-HDL-C;

Low-density lipoprotein cholesterol is determined by preparative ultracentrifugation; Percent change from baseline to Week 12 in TC, LDL-C, free fatty acids (FFAs), Apo A2, Apo B, Apo B48, Apo B100, Apo C2, Apo C3, and Apo E;

Change from baseline to Week 12 in fibroblast growth factor 21 (FGF21) and high-sensitivity C-reactive protein (hsCRP), and percent change from baseline to Week 12 in ion mobility analysis and lipoprotein fraction (nuclear magnetic resonance [NMR]); and Percent change from baseline to Week 12 in the lipid and lipoprotein ratios of TG:HDL-C, TC:HDL-C, non-HDL-C:HDL-C, LDL-C:Apo B, Apo B:Apo A1, and Apo C3:Apo C2.

The secondary efficacy endpoints for the 40-week Extension Period include the following:

Percent change from baseline to Week 52 in fasting TG;

Percent change from baseline to Week 52 in remnant cholesterol (calculated as TC-LDL-C-HDL-C), HDL-C, Apo A1, and non-HDL-C;

Low-density lipoprotein cholesterol is determined by preparative ultracentrifugation;

Percent change from baseline to Week 52 in TC, LDL-C, FFAs, Apo A2, Apo B, Apo B48, Apo B100, Apo C2, Apo C3, and Apo E;

Change from baseline to Week 52 in FGF21 and hsCRP, and percent change from baseline to Week 52 in ion mobility analysis and lipoprotein fraction (NMR); and Percent change from baseline to Week 52 in the lipid and lipoprotein ratios of TG:HDL-C, TC:HDL-C, non-HDL-C:HDL-C, LDL-C:Apo B, Apo B:Apo A1, and Apo C3:Apo C2.

Baseline for TG, TC, HDL-C, non-HDL-C, LDL-C, and remnant cholesterol are defined as the mean of Visit 4 (Day 1) and the preceding TG qualifying visit (either Visit 3 [Week −1] or Visit 3.1, if required) measurements. Baseline for all other efficacy and safety variables are defined as Visit 4 (Day 1). If the measurement at this visit is missing, the last measurement prior to the first dose of randomized study drug is used.

For patients randomized to receive placebo (in the 12-week Efficacy Period) and fenofibrate 145 mg (in the 40-week Extension Period), change from Visit 7 (Week 12) in efficacy and safety variables also are explored.

The exploratory efficacy endpoints for the 12-week Efficacy Period include the following:

Change from baseline to Week 12 in selected biomarkers suggestive of hepatic inflammation and fibrosis, including cytokeratin-18 (CK-18), ferritin, hyaluronic acid, tumor necrosis factor alpha (TNF-α), type IV collagen, and adiponectin.

The exploratory efficacy endpoints for the 40-week Extension Period include the following:

Change from baseline to Week 52 in selected biomarkers suggestive of hepatic inflammation and fibrosis, including CK-18, ferritin, hyaluronic acid, TNF-α, type IV collagen, and adiponectin.

Safety:

Safety assessments include adverse events (AEs), clinical laboratory measurements (chemistry, hematology, coagulation profile, endocrinology, and urinalysis), 12-lead electrocardiograms (ECGs), vital signs (heart rate, respiratory rate, and blood pressure), and physical examinations.

Pharmacokinetics/Pharmacodynamics:

Pharmacokinetic concentrations collected during the 12-week Efficacy Period is used for population PK analysis and PK/PD analysis.

Inclusion Criteria:

Able to understand and willing to comply with all study requirements and procedures throughout the duration of the study and give written informed consent;

Aged ≥18 years;

Patients receiving statin therapy must meet one of the following criterial:

Aged ≥21 years with clinical atherosclerotic cardiovascular disease (ASCVD) (history of acute coronary syndrome or myocardial infarction, stable or unstable angina, coronary revascularization, stroke, transient ischemic attack [TIA] presumed to be of atherosclerotic origin, or peripheral arterial disease or revascularization), on a high intensity statin (or moderate intensity statin if not a candidate for high intensity statin due to safety concerns);

Aged ≥21 years with a history of LDLC≥190 mg/dL, which is not due to secondary modifiable causes, on a high intensity statin (or moderate intensity statin if not a candidate for high intensity statin due to safety concerns);

Aged 40 to 75 years, inclusive, without clinical ASCVD but with diabetes and a history of LDLC of 70 to 189 mg/dL, inclusive, on a moderate or high intensity statin; or Aged 40 to 75 years, inclusive, without clinical ASCVD or diabetes, with a history of LDLC of 70 to 189 mg/dL, inclusive, with estimated 10 year risk for ASCVD of ≥7.5% by the Pooled Cohort Equation on a moderate or high intensity statin;

Patients not currently on statins, must not meet the criteria for statin therapy listed above;

Exclusion Criteria:

Patients who require lipid altering treatments other than study drugs (pemafibrate or fenofibrate), statins, ezetimibe, or PCSK9 inhibitors during the course of the study. These include bile acid sequestrants, non-study fibrates, niacin (>100 mg/day), omega 3 fatty acids (>1000 mg/day), or any supplements used to alter lipid metabolism including, but not limited to, red rice yeast supplements, garlic supplements, soy isoflavone supplements, sterol/stanol products, or policosanols;

Body mass index (BMI)>45 kg/m2 at Visit 1 (Week 8 or Week 6);

Patients with type 1 diabetes mellitus;

Patients with newly diagnosed (within 3 months prior to Visit 2 [Week 2])

or poorly controlled type 2 diabetes mellitus (T2DM), defined as hemoglobin A1c>9.5% at Visit 1 (Week 8 or Week 6);

Statistical Analysis:

Efficacy:

In order to control the family-wise Type I error at a 0.05 level, a fixed sequential testing procedure is implemented. In a hierarchical step-down manner, the primary endpoint is tested first, followed by secondary endpoints, tested in the following hierarchical manner: percent change from baseline to Week 12 in a fixed sequence of (1) remnant cholesterol (calculated as TC-LDL-C-HDL-C), (2) HDL-C, (3) Apo A1, and (4) non-HDL-C. Each test is planned to be performed at a 0.05 significance level. Inferential conclusions about these efficacy endpoints require statistical significance of the previous one.

For other efficacy endpoints, nominal p-values and 95% confidence intervals (CIs) is presented, but should not be considered as confirmatory.

The primary efficacy analysis is based on Hodges-Lehmann estimator with pattern-mixture model imputation based on the Full Analysis Set (FAS). The pattern-mixture model is used as the primary imputation method as part of the primary analysis for the percent change in fasting TGs from baseline to Week 12. This imputation model includes factors such as patient demographics, disease status, and baseline TG, as well as adherence to therapy. The imputation model imputes missing Week 12 TG values as follows:

For patients who do not adhere to therapy and who do not have a Week 12 measurement, the missing data imputation method use patients in the same treatment arm who do not adhere to therapy and have a Week 12 measurement; and If there are no patients in the same treatment arm who do not adhere to therapy and have a Week 12 measurement, missing Week 12 TG values are imputed as follows:

For the pemafibrate arm, the treatment effect is considered washed out and baseline TG values are used to impute the Week 12 TG values; and For the placebo arm, missing Week 12 TG values are imputed assuming missing at random, including patient demographics, disease status, and baseline and post-baseline efficacy data from the placebo arm.

After the multiple imputation step, each imputed dataset is analyzed by the nonparametric Hodges-Lehmann method and the Hodges-Lehmann estimator and standard error are combined to produce treatment difference estimate and 95% CI and p-value.

Other sensitivity methods are to be explored including (1) Hodges-Lehmann estimator with imputation method probabilities of missing estimated using logistic regression based on the FAS and (2) analysis of covariance (ANCOVA) of rank-transformed Week 12 percent change from baseline in TG with pattern-mixture model imputation based on the FAS. Additional statistical methods might be explored, including mixed effect model repeat measurement (MMRM) with percent change in TG from baseline based on the FAS.

The primary efficacy analysis is repeated on the Per-Protocol Set.

Summary statistics (number of patients, mean, standard deviation, median, minimum, maximum, $25^{th}$ percentile, and $75^{th}$ percentile) at baseline, each scheduled visit, and change and percent change in fasting TG from baseline to each scheduled visit is provided.

Secondary efficacy endpoints included in the hierarchical step-down testing procedure include percent change from baseline to Week 12 in a fixed sequence of (1) remnant cholesterol, (2) HDL-C, (3) Apo A1, and (4) non-HDL-C.

The secondary and exploratory efficacy endpoints during the 12-week Efficacy Period is analyzed using an ANCOVA model with the same imputation method used for the primary analysis. The ANCOVA model includes country, current statin therapy use (not on statin therapy versus currently receiving statin therapy), and treatment as factors; baseline value as a covariate.

If the normality assumption is not met, the Hodges-Lehmann estimator with the same imputation method used for the primary analysis is used.

The secondary efficacy endpoint of percent change in fasting TG from baseline to Week 52 is summarized descriptively. Change from Visit 7 (Week 12) for the fenofibrate group during the 40-week Extension Period also is summarized for each visit. Other efficacy endpoints during the 40-week Extension Period will be summarized descriptively. No hypothesis testing is performed.

Analyses of selected primary, secondary, and exploratory efficacy variables may be performed for subgroups of patients based on statin therapy (statin therapy versus no statin therapy), gender, age (<65 years versus ≥65 years), race (white versus not white), ethnicity, and other baseline characteristics.

Safety:

The safety endpoint data are summarized for the Safety Analysis Set for the 12-week Efficacy Period, 40-week Extension Period, and overall.

The AEs are coded using the latest version of the Medical Dictionary for Regulatory Activities. A general summary of the AEs and serious AEs (SAEs) are summarized by overall number of AEs, severity, and relationship to study drug per treatment group. The number of AEs leading to withdrawal and SAEs leading to death also are summarized. The incidence of AEs is summarized by body system and treatment group. The incidence of treatment-emergent AEs also is summarized by system organ class and preferred term.

The safety laboratory data are summarized by visit and by treatment group, along with changes from the baseline. The values that are below the lower limit or above the upper limit of the reference range are flagged. Those values or changes in values that are identified as being clinically significant are flagged. Laboratory abnormalities of special interest, such as liver function tests and pancreatitis events, are summarized.

Vital signs and 12-lead ECGs also are summarized by visit and by treatment group, along with the changes from baseline.

Pharmacokinetics:

Population PK and PK/PD data are analyzed and reported separately. The concentration-time data are modeled using a population approach with compartment models, and the effects of patient characteristics are examined to determine if they influence drug exposure. Patient characteristics are include age, gender, ethnicity, BMI, country, etc. In addition, the relationship between drug concentration and safety variables are investigated. Safety variables include, but are not limited to, AST, ALT, alkaline phosphatase, and CK. Measures of exposure (predicted clearance, area under the concentration-time curve [AUC], and/or maximum plasma PK concentration [$C_{max}$]) are correlated with safety variables.

Example 2 Treatment of Severe Hypertriglyceridemia with Pemafibrate

Title of Study:

A Phase 3, Multi-Center, Placebo-Controlled, Randomized, Double-Blind, 12-Week Study With a 40-Week, Active-Controlled, Double-Blind Extension to Evaluate the Efficacy and Safety of Pemafibrate in Adult Patients With Fasting Triglyceride Levels ≥500 mg/dL and <2000 mg/dL and Mild or Moderate Renal Impairment.

Study Design:

Study K-877-303 is a Phase 3, multi-center, randomized, study to confirm the efficacy and safety of pemafibrate 0.2 mg twice daily compared to matching placebo (in the double-blind 12-week Efficacy Period) and an active comparator, fenofibrate (in the open-label 40-week Extension Period), in patients with fasting triglyceride (TG) levels ≥500 mg/dL (5.65 mmol/L) and <2000 mg/dL (22.60 mmol/L) and mild or moderate renal impairment (estimated glomerular filtration rate [eGFR]≥30 mL/min/1.73 m² and <90 mL/min/1.73 m²).

Eligible patients enter a 4- to 6-week lifestyle stabilization period (4-week stabilization for patients not requiring washout and 6-week washout and stabilization for patients on lipid-altering therapy other than statins, ezetimibe, or proprotein convertase subtilisin/kexin type 9 [PCSK9] inhibitors). The stabilization period is followed by a 2-week TG qualifying period (Visits 2 [Week −2] and 3 [Week −1]), and patient eligibility is assessed based on the mean TG value from these 2 visits. If the patient's mean TG level during the TG qualifying period is ≥450 mg/dL (5.09 mmol/L) and <500 mg/dL (5.65 mmol/L), an additional TG measurement can be taken 1 week later at Visit 3.1. The mean of all 3 TG measurements is used to determine eligibility for the study. After confirmation of qualifying fasting TG values, eligible patients enter a 12-week, randomized, double-blind Efficacy Period. At Visit 4 (Day 1), patients are randomly assigned in a 2:1 ratio to pemafibrate 0.2 mg twice daily or identical matching placebo tablets twice daily. During the 12-week Efficacy Period, patients return to the site at Visit 5 (Week 4), Visit 6 (Week 8), and Visit 7 (Week 12) for efficacy and safety evaluations.

Patients who successfully complete the 12-week Efficacy Period are eligible to continue in a 40-week, open-label, active-controlled Extension Period after completing the Visit 7 (Week 12) procedures. Patients randomized to receive pemafibrate 0.2 mg twice daily in the 12-week Efficacy Period continue to receive pemafibrate 0.2 mg twice daily in the 40-week Extension Period. Patients randomized to receive placebo matching pemafibrate 0.2 mg twice daily in the 12-week Efficacy Period initiate fenofibrate dosing at 48 mg once daily at Visit 7 (Week 12). Starting from Visit 8 (Week 16), Investigators can adjust fenofibrate dosing (to 145 mg once daily) at their discretion according to the local standard of care.

From Visit 7 (Week 12), patients not on statins, ezetimibe, or PCSK9 inhibitors may initiate therapy, and patients receiving statins, ezetimibe, or PCSK9 inhibitors may alter their dose, as indicated by guidelines or local standard of care.

After Visit 8 (Week 16), patients are to return to the site every 12 weeks until the last visit (Visit 11 [Week 52]).

Primary Objective:

The primary objective of the study is to demonstrate the efficacy of pemafibrate 0.2 mg twice daily compared to placebo from baseline to Week 12 in lowering fasting TG levels in patients with fasting TG levels ≥500 mg/dL (5.65 mmol/L) and <2000 mg/dL (22.60 mmol/L) and mild or moderate renal impairment.

Secondary Objectives:

The secondary objectives of the study are the following:
- To evaluate the efficacy of pemafibrate 0.2 mg twice daily from baseline to Week 52 in lowering fasting TG levels in patients with fasting TG levels ≥500 mg/dL (5.65 mmol/L) and <2000 mg/dL (22.60 mmol/L) and mild or moderate renal impairment;
- To evaluate the efficacy of pemafibrate 0.2 mg twice daily from baseline to Week 12 and Week 52 in altering lipid parameters in patients with fasting TG levels ≥500 mg/dL (5.65 mmol/L) and <2000 mg/dL (22.60 mmol/L) and mild or moderate renal impairment;
- To evaluate the safety and tolerability of pemafibrate 0.2 mg twice daily in patients with fasting TG levels ≥500 mg/dL (5.65 mmol/L) and <2000 mg/dL (22.60 mmol/L) and mild or moderate renal impairment; and To determine the plasma concentrations of pemafibrate for the purpose of use in population pharmacokinetic (PK) analysis and PK/pharmacodynamic (PD) analysis.

Exploratory Objective:

The exploratory objective of the study is to evaluate signs of potential efficacy of pemafibrate 0.2 mg twice daily in treating non-alcoholic fatty liver disease in patients with fasting TG levels ≥500 mg/dL (5.65 mmol/L) and <2000 mg/dL (22.60 mmol/L) and mild or moderate renal impairment.

Patient Population:

The study population consist of male and female patients ≥18 years of age with fasting TG levels ≥500 mg/dL (5.65 mmol/L) and <2000 mg/dL (22.60 mmol/L) after washout from background lipid-altering therapy other than statins, ezetimibe, or PCSK9 inhibitors and with normal renal function. Stable therapy with statins, ezetimibe, or PCSK9 inhibitors is allowed. The 40-week, active-controlled Extension Period population consists of patients completing the 12-week placebo-controlled Efficacy Period. Patients in the 40-week, active-controlled Extension Period are allowed to continue in the study even if the background lipid-altering therapy with statins, ezetimibe, or PCSK9 inhibitors requires adjustment.

Number of Patients:

Approximately 420 patients (280 patients receiving pemafibrate; 140 patients receiving placebo/fenofibrate)

Dose Levels:

12-Week Efficacy Period

Pemafibrate: 0.2 mg twice daily

Placebo: twice daily

40-Week Extension Period

Pemafibrate: 0.2 mg twice daily/fenofibrate matching placebo: once daily

Fenofibrate: 48 mg once daily or 145 mg once daily/Pemafibrate matching placebo: twice daily Route of Administration:

Oral

Duration of Treatment:

This study consists of a 12-week, double-blind, placebo-controlled Efficacy Period, followed by a 40-week, double-blind, active-controlled Extension Period, for a total of 52 weeks on study drug.

Criteria for Evaluation:

Efficacy:

The primary efficacy endpoint is the percent change in fasting TG from baseline to Week 12. Baseline for TG is defined as the mean of Visit 4 (Day 1) and the preceding TG qualifying visit (either Visit 3 [Week −1] or Visit 3.1, if required) measurements.

The secondary efficacy endpoints for the 12-week Efficacy Period include the following:

Percent change from baseline to Week 12 in remnant cholesterol (calculated as total cholesterol [TC]-low-density lipoprotein C [LDL-C]-high-density lipoprotein C [HDL-C]), HDL-C, apolipoprotein (Apo) A1, and non-HDL-C;

Low-density lipoprotein cholesterol is determined by preparative ultracentrifugation;

Percent change from baseline to Week 12 in TC, LDL-C, free fatty acids (FFAs), Apo A2, Apo B, Apo B48, Apo B100, Apo C2, Apo C3, and Apo E;

Change from baseline to Week 12 in fibroblast growth factor 21 (FGF21) and high-sensitivity C-reactive protein (hsCRP), and percent change from baseline to Week 12 in ion mobility analysis and lipoprotein fraction (nuclear magnetic resonance [NMR]); and Percent change from baseline to Week 12 in the lipid and lipoprotein ratios of TG:HDL-C, TC:HDL-C, non-HDL-C:HDL-C, LDL-C:Apo B, Apo B:Apo A1, and Apo C3:Apo C2.

The secondary efficacy endpoints for the 40-week Extension Period include the following:

Percent change from baseline to Week 52 in fasting TG;

Percent change from baseline to Week 52 in remnant cholesterol (calculated as TC-LDL-C-HDL-C), HDL-C, Apo A1, and non-HDL-C;

Low-density lipoprotein cholesterol is determined by preparative ultracentrifugation;

Percent change from baseline to Week 52 in TC, LDL-C, FFAs, Apo A2, Apo B, Apo B48, Apo B100, Apo C2, Apo C3, and Apo E;

Change from baseline to Week 52 in FGF21 and hsCRP, and percent change from baseline to Week 52 in ion mobility analysis and lipoprotein fraction (NMR); and Percent change from baseline to Week 52 in the lipid and lipoprotein ratios of TG:HDL-C, TC:HDL-C, non-HDL-C:HDL-C, LDL-C:Apo B, Apo B:Apo A1, and Apo C3:Apo C2.

Baseline for TG, TC, HDL-C, non-HDL-C, LDL-C, and remnant cholesterol are defined as the mean of Visit 4 (Day 1) and the preceding TG qualifying visit (either Visit 3 [Week −1] or Visit 3.1, if required) measurements. Baseline for all other efficacy and safety variables are defined as Visit 4 (Day 1). If the measurement at this visit is missing, the last measurement prior to the first dose of randomized study drug is used.

For patients randomized to receive placebo (in the 12-week Efficacy Period) and fenofibrate (in the 40-week Extension Period), change from Visit 7 (Week 12) in efficacy and safety variables also are explored.

The exploratory efficacy endpoints for the 12-week Efficacy Period include the following:

Change from baseline to Week 12 in selected biomarkers suggestive of hepatic inflammation and fibrosis, including cytokeratin-18 (CK-18), ferritin, hyaluronic acid, tumor necrosis factor alpha (TNF-α), type IV collagen, and adiponectin.

The exploratory efficacy endpoints for the 40-week Extension Period include the following:

Change from baseline to Week 52 in selected biomarkers suggestive of hepatic inflammation and fibrosis, including CK-18, ferritin, hyaluronic acid, TNF-α, type IV collagen, and adiponectin.

Safety:

Safety assessments include adverse events (AEs), clinical laboratory measurements (chemistry, hematology, coagulation profile, endocrinology, and urinalysis), 12-lead electrocardiograms (ECGs), vital signs (heart rate, respiratory rate, and blood pressure), and physical examinations.

Pharmacokinetics/Pharmacodynamics:

Pharmacokinetic concentrations collected during the 12-week Efficacy Period is used for population PK analysis and PK/PD analysis.

Inclusion Criteria:

Able to understand and willing to comply with all study requirements and procedures throughout the duration of the study and give written informed consent;

Aged ≥18 years;

Patients receiving statin therapy must meet one of the following criteria:
  Aged ≥21 years with clinical atherosclerotic cardiovascular disease (ASCVD) (history of acute coronary syndrome or myocardial infarction, stable or unstable angina, coronary revascularization, stroke, transient ischemic attack [TIA] presumed to be of atherosclerotic origin, or peripheral arterial disease or revascularization), on a high intensity statin (or moderate intensity statin if not a candidate for high intensity statin due to safety concerns);
  Aged ≥21 years with a history of LDLC≥190 mg/dL, which is not due to secondary modifiable causes, on a high intensity statin (or moderate intensity statin if not a candidate for high intensity statin due to safety concerns);
  Aged 40 to 75 years, inclusive, without clinical ASCVD but with diabetes and a history of LDLC of 70 to 189 mg/dL, inclusive, on a moderate or high intensity statin; or
  Aged 40 to 75 years, inclusive, without clinical ASCVD or diabetes, with a history of LDLC of 70 to 189 mg/dL, inclusive, with estimated 10 year risk for ASCVD of ≥7.5% by the Pooled Cohort Equation on a moderate or high intensity statin;
  Patients not currently on statins, must not meet the criteria for statin therapy listed above;
  Fasting TG levels ≥500 mg/dL (5.65 mmol/L) and <2000 mg/dL (22.60 mmol/L) based on the mean of Visit 2 (Week −2) and Visit 3 (Week-1);
  Normal renal function (i.e., estimated glomerular filtration rate [eGFR]≥90 mL/min/1.73 m2) at Visit 1 (Week −8 or Week −6);
Exclusion Criteria:
  Patients who require lipid altering treatments other than study drugs (pemafibrate or fenofibrate), statins, ezetimibe, or PCSK9 inhibitors during the course of the study. These include bile acid sequestrants, non-study fibrates, niacin (>100 mg/day), omega 3 fatty acids (>1000 mg/day), or any supplements used to alter lipid metabolism including, but not limited to, red rice yeast supplements, garlic supplements, soy isoflavone supplements, sterol/stanol products, or policosanols;
  Body mass index (BMI)>45 kg/m2 at Visit 1 (Week 8 or Week 6);
  Patients with type 1 diabetes mellitus;
  Patients with newly diagnosed (within 3 months prior to Visit 2 [Week 2]) or poorly controlled type 2 diabetes mellitus (T2DM), defined as hemoglobin A1c>9.5% at Visit 1 (Week 8 or Week 6);
Statistical Analysis:
Efficacy:
  In order to control the family-wise Type I error at a 0.05 level, a fixed sequential testing procedure is implemented. In a hierarchical step-down manner, the primary endpoint is tested first, followed by secondary endpoints, tested in the following hierarchical manner: percent change from baseline to Week 12 in a fixed sequence of (1) remnant cholesterol (calculated as TC-LDL-C-HDL-C), (2) HDL-C, (3) Apo A1, and (4) non-HDL-C. Each test is planned to be performed at a 0.05 significance level. Inferential conclusions about these efficacy endpoints require statistical significance of the previous one.
  For other efficacy endpoints, nominal p-values and 95% confidence intervals (CIs) is presented, but should not be considered as confirmatory.

The primary efficacy analysis is based on Hodges-Lehmann estimator with pattern-mixture model imputation based on the Full Analysis Set (FAS). The pattern-mixture model is used as the primary imputation method as part of the primary analysis for the percent change in fasting TGs from baseline to Week 12. This imputation model includes factors such as patient demographics, disease status, and baseline TG, as well as adherence to therapy. The imputation model imputes missing Week 12 TG values as follows:
  For patients who do not adhere to therapy and who do not have a Week 12 measurement, the missing data imputation method use patients in the same treatment arm who do not adhere to therapy and have a Week 12 measurement; and
  If there are no patients in the same treatment arm who do not adhere to therapy and have a Week 12 measurement, missing Week 12 TG values are imputed as follows:
    For the pemafibrate arm, the treatment effect is considered washed out and baseline TG values are used to impute the Week 12 TG values; and
    For the placebo arm, missing Week 12 TG values are imputed assuming missing at random, including patient demographics, disease status, and baseline and post-baseline efficacy data from the placebo arm.
  After the multiple imputation step, each imputed dataset is analyzed by the nonparametric Hodges-Lehmann method and the Hodges-Lehmann estimator and standard error are combined to produce treatment difference estimate and 95% CI and p-value.
  Other sensitivity methods are to be explored including (1) Hodges-Lehmann estimator with imputation method probabilities of missing estimated using logistic regression based on the FAS and (2) analysis of covariance (ANCOVA) of rank-transformed Week 12 percent change from baseline in TG with pattern-mixture model imputation based on the FAS. Additional statistical methods might be explored, including mixed effect model repeat measurement (MMRM) with percent change in TG from baseline based on the FAS.
  The primary efficacy analysis is repeated on the Per-Protocol Set.
  Summary statistics (number of patients, mean, standard deviation, median, minimum, maximum, $25^{th}$ percentile, and $75^{th}$ percentile) at baseline, each scheduled visit, and change and percent change in fasting TG from baseline to each scheduled visit is provided.
  Secondary efficacy endpoints included in the hierarchical step-down testing procedure include percent change from baseline to Week 12 in a fixed sequence of (1) remnant cholesterol, (2) HDL-C, (3) Apo A1, and (4) non-HDL-C.
  The secondary and exploratory efficacy endpoints during the 12-week Efficacy Period is analyzed using an ANCOVA model with the same imputation method used for the primary analysis. The ANCOVA model includes country, current statin therapy use (not on statin therapy versus currently receiving statin therapy), and treatment as factors; baseline value as a covariate. If the normality assumption is not met, the Hodges-Lehmann estimator with the same imputation method used for the primary analysis is used.
  The secondary efficacy endpoint of percent change in fasting TG from baseline to Week 52 is summarized descriptively. Change from Visit 7 (Week 12) for the fenofibrate group during the 40-week Extension Period also is summarized for each visit. Other efficacy endpoints during the 40-week Extension Period will be summarized descriptively. No hypothesis testing is performed.

Analyses of selected primary, secondary, and exploratory efficacy variables may be performed for subgroups of patients based on statin therapy (statin therapy versus no statin therapy), gender, age (<65 years versus ≥65 years), race (white versus not white), ethnicity, and other baseline characteristics.

Safety:

The safety endpoint data are summarized for the Safety Analysis Set for the 12-week Efficacy Period, 40-week Extension Period, and overall.

The AEs are coded using the latest version of the Medical Dictionary for Regulatory Activities. A general summary of the AEs and serious AEs (SAEs) are summarized by overall number of AEs, severity, and relationship to study drug per treatment group. The number of AEs leading to withdrawal and SAEs leading to death also are summarized. The incidence of AEs is summarized by body system and treatment group. The incidence of treatment-emergent AEs also is summarized by system organ class and preferred term.

The safety laboratory data are summarized by visit and by treatment group, along with changes from the baseline. The values that are below the lower limit or above the upper limit of the reference range are flagged. Those values or changes in values that are identified as being clinically significant are flagged. Laboratory abnormalities of special interest, such as liver function tests and pancreatitis events, are summarized.

Vital signs and 12-lead ECGs also are summarized by visit and by treatment group, along with the changes from baseline.

Pharmacokinetics:

Population PK and PK/PD data are analyzed and reported separately. The concentration-time data are modeled using a population approach with compartment models, and the effects of patient characteristics are examined to determine if they influence drug exposure. Patient characteristics are include age, gender, ethnicity, BMI, country, etc. In addition, the relationship between drug concentration and safety variables are investigated. Safety variables include, but are not limited to, AST, ALT, alkaline phosphatase, and CK. Measures of exposure (predicted clearance, area under the concentration-time curve [AUC], and/or maximum plasma PK concentration [$C_{max}$]) are correlated with safety variables.

Example 3. Long-Term Efficacy and Safety of Pemafibrate in Dyslipidemic Patients with Renal Impairment This was a multicenter, single-arm, open-label, phase III trial. The inclusion criteria were as follows: (1) patients with dyslipidemia aged >20 years at the time of informed consent; (2) men and postmenopausal women; (3) fasting serum TG≥1.70 mmol/L (150 mg/dL) at two consecutive measurements during screening; and (4) patients who followed dietary and physical exercise guidance for >12 weeks before enrollment.

The major exclusion criteria were as follows: (1) patients with fasting serum TG≥5.65 mmol/L (500 mg/dL) during screening; (2) patients with poorly controlled diabetes mellitus (hemoglobin A1c [HbA1c]≥10.5%); (3) patients with concurrent poorly controlled thyroid disease; (4) men with serum creatinine ≥2.5 mg/dL and women with serum creatinine ≥2.0 mg/dL during screening who were already on statin therapy; (5) patients with eGFR<45 mL/min/1.73 m² during screening who were already on statin therapy; (6) patients with CK>5ULN (270 IU/L for men, 150 IU/L for women) during screening who were already on statin therapy; (7) patients with serious liver disease (cirrhosis Child-Pugh Class B or higher); (8) patients with gallstones or serious biliary tract disease; (9) patients who had suffered an acute myocardial infarction or stroke within three months before informed consent; and (10) patients with New York Heart Association class III or IV heart failure.

During the screening period (8 weeks prior to treatment initiation), tests were performed twice to determine patient eligibility. Thereafter, eligible patients orally received pemafibrate 0.2 mg/day (twice daily) for 52 weeks. From week 12 of the treatment period onwards, the investigators were instructed that the dose could be increased from 0.2 mg/day to 0.4 mg/day (twice daily) if there was an inadequate response to the initial dose based on fasting serum TG levels ≥1.70 mmol/L (150 mg/dL). Fasting blood and urine samples were collected at each visit. Blood and urine sample in patients with hemodialysis were collected just before dialysis. LDL-C levels were measured using the direct method. Lipoprotein fractions were measured by HPLC at baseline and weeks 12 and 40.

The primary efficacy endpoint was the percent change in fasting serum TG from baseline to the last evaluation point. The primary safety endpoints were the incidence of an AE or ADR occurring after drug administration during the study. Secondary efficacy endpoints included percent changes in lipid variables and changes in inflammation variables at week 52 [using the last-observation-carried-forward (LOCF)]. Secondary safety endpoints included changes in the levels of aspartate aminotransferase (AST), ALT, -GT, ALP, serum creatinine, eGFR, and CK at week 52. Each baseline value was defined as (1) the mean of the corresponding values in the first and second tests at the screening examination and at week 0 of the treatment period for fasting serum TG, HDL-C, total cholesterol (TC), LDL-C, and non-HDL-C; and (2) the value at week 0 of the treatment period for the other secondary variables. Efficacy and safety were established post hoc by subgroups stratified by baseline eGFR as follows: G1 (normal or high; ≥90 mL/min/1.73 m2), G2 (mildly decreased; ≥60 and <90 mL/min/1.73 m2), G3a-G3b (mildly to moderately decreased and moderately to severely decreased; ≥30 and <60 mL/min/1.73 m2), and G4-G5 (severely decreased and kidney failure; <30 mL/min/1.73 m2), according to the Kidney Disease Improving Global Outcomes (KDIGO) 2012 Clinical Practice Guideline for the Evaluation and Management of Chronic Kidney Disease.

The plasma concentration of pemafibrate was measured with liquid chromatography-tandem mass spectrometry (LC-MS-MS) only at the institutions where this procedure was feasible and in patients who provided informed consent. Blood sampling for trough values was conducted before the morning dose of pemafibrate in parallel with that for fasting blood laboratory tests in weeks 4, 8, and 12 of the treatment period. Blood sampling after pemafibrate administration was carried out once between weeks 4 and 24 at 0.5-1.5, 1.5-3, and 4-6 h after pemafibrate administration.

The target sample size was set to 170 patients based on the number required to evaluate safety according to the International Conference on Harmonisation (ICH)-E1 guideline "Extent of population exposure to assess clinical safety for drugs intended for long-term treatment of non-life-threatening conditions". For the primary efficacy endpoint, one-sample t-tests were performed.

The numbers of patients with AEs and ADRs and the incidences of AEs and ADRs were calculated in the analysis of primary safety endpoints. For the secondary efficacy endpoints, one-sample t-tests or Wilcoxon signed-rank tests

[for high-sensitivity C-reactive protein (hsCRP) and IL-1] were performed. The secondary safety endpoints were analyzed with Wilcoxon signed-rank tests. A two-sided significance level of 0.05 was used. SAS v. 9.3 (SAS Institute Inc., Cary, N.C., USA) was used for these analyses. Where indicated, the data are expressed as means±standard deviation (SD).

Results are presented in Tables 1-3:

TABLE 1

Changes from baseline in lipid levels and inflammatory parameters during the 52-weeek treatment period.

| Parameter | | All Participants | Baseline eGFR Category | | | |
| --- | --- | --- | --- | --- | --- | --- |
| | | | G1 | G2 | G3a-G3b | G4-G5 |
| TG (mmol/L) | n | 189 | 21 | 123 | 24 | 8 |
| | Baseline | 2.82 (0.88) | 2.94 (1.03) | 2.80 (0.89) | 2.88 (0.86) | 2.72 (0.47) |
| | Week 52 (LOCF) | 1.48 (0.69) | 1.71 (0.87) | 1.47 (0.72) | 1.36 (0.44) | 1.64 (0.54) |
| | % Change | −45.8 (21.8) *** | −41.4 (23.0) *** | −45.8 (23.1) *** | −51.1 (15.4) *** | −37.7 (23.6) ** |
| HDL-C (mmol/L) | n | 189 | 21 | 123 | 34 | 8 |
| | Baseline | 1.18 (0.27) | 1.24 (0.36) | 1.19 (0.24) | 1.19 (0.31) | 0.87 (0.22) |
| | Week 52 (LOCF) | 1.33 (0.34) | 1.29 (0.44) | 1.34 (0.32) | 1.38 (0.35) | 1.18 (0.37) |
| | % Change | 13.1 (17.1) *** | 3.6 (16.9) | 11.9 (16.2) *** | 17.0 (13.0) *** | 34.1 (23.7) ** |
| TG/HDL-C [(mmol/L)/(mmol/L)] | n | 189 | 21 | 123 | 34 | 8 |
| | Baseline | 2.58 (1.22) | 2.69 (1.52) | 2.49 (1.13) | 2.69 (1.37) | 3.30 (0.95) |
| | Week 52 (LOCF) | 2.27 (0.85) | 1.58 (1.03) | 1.24 (0.87) | 1.09 (0.55) | 1.68 (1.12) |
| | % Change | −49.7 (25.7) *** | −40.5 (38.2) *** | −48.9 (26.5) *** | −57.0 (15.9) *** | −51.0 (22.4) *** |
| LDL-C (mmol/L) | n | 189 | 21 | 123 | 34 | 8 |
| | Baseline | 3.09 (0.82) | 3.20 (0.88) | 3.08 (0.78) | 2.96 (0.72) | 3.42 (1.18) |
| | Week 52 (LOCF) | 3.02 (0.75) | 3.12 (0.89) | 3.03 (0.25) | 2.97 (0.62) | 2.82 (0.85) |
| | % Change | 2.2 (30.4) | 2.7 (33.7) | 2.1 (29.2) | 5.1 (30.0) | −8.8 (41.2) |
| non-HDL-C (mmol/L) | n | 189 | 21 | 123 | 34 | 8 |
| | Baseline | 4.03 (0.79) | 4.18 (0.87) | 4.00 (0.73) | 3.92 (0.61) | 4.54 (1.34) |
| | Week 52 (LOCF) | 3.63 (0.83) | 3.77 (1.04) | 3.64 (0.85) | 3.56 (0.66) | 3.48 (0.96) |
| | % Change | −8.7 (18.8) *** | −8.3 (21.1) | −8.4 (17.4) *** | −7.7 (18.0) * | −17.3 (33.5) |
| RemL-C (mmol/L) | n | 187 | 21 | 122 | 34 | 7 |
| | Baseline | 0.48 (0.26) | 0.54 (0.30) | 0.46 (0.26) | 0.48 (0.26) | 0.59 (0.15) |
| | Week 52 (LOCF) | 0.18 (0.13) | 0.21 (0.15) | 0.18 (0.14) | 0.17 (0.09) | 0.24 (0.17) |
| | % Change | −57.2 (28.7) *** | −59.9 (21.1) *** | −56.0 (31.8) *** | −59.3 (22.9) *** | −57.1 (25.8) ** |
| apoA1 (mg/dL) | n | 187 | 21 | 122 | 34 | 7 |
| | Baseline | 131.6 (19.8) | 184.2 (22.0) | 182.2 (18.2) | 133.5 (20.0) | 105.4 (19.7) |
| | Week 52 (LOCF) | 137.6 (22.4) | 133.8 (26.0) | 137.2 (20.0) | 144.0 (25.5) | 122.4 (20.8) |
| | % Change | 5.0 (11.2) *** | 0.0 (13.9) | 4.1 (10.5) *** | 8.0 (10.0) *** | 16.7 (10.6) ** |

Observations:

The lowest eGFR group (eGFR<30 mL/min/1.73 m$^2$:G4-G5) experienced a reduction in LDL-C, contrary to results previously reported for pemafibrate.

TABLE 2

Changes from baseline in the levels of cholesterol in CM, VLDL, LDL, and HDL subclasses measured by HPLC.

| Parameter | | All Participants | Bine eGFR Category | | | |
| --- | --- | --- | --- | --- | --- | --- |
| (mmol/L) | n | 188 | G1 | G2 | G3a-G3b | G4-G5 |
| | | | 21 | 123 | 34 | 7 |
| CM-C | Baseline | 0.154 (0.135) | 0.158 (0.114) | 0.151 (0.146) | 0.156 (0.121) | 0.188 (0.082) |
| | Week 52 (LOCF) | 0.039 (0.038) | 0.064 (0.055) | 0.038 (0.036) | 0.038 (0.025) | 0.039 (0.037) |
| | % Change | −64.3 (35.5) *** | −54.1 (46.0) *** | −63.9 (36.1) *** | −67.7 (29.1) *** | −79.4 (14.0) *** |
| VLDL-C | Baseline | 1.196 (0.335) | 1.260 (0.390) | 1.164 (0.300) | 1.177 (0.319) | 1.559 (0.474) |
| | Week 52 (LOCF) | 0.866 (0.264) | 0.932 (0.323) | 0.834 (0.234) | 0.892 (0.293) | 1.076 (0.372) |
| | % Change | −24.9 (22.5) *** | −24.6 (20.0) *** | −25.3 (22.9) *** | −22.9 (21.5) *** | −28.7 (25.5) * |
| Large LDL-C | Baseline | 0.504 (0.185) | 0.529 (0.186) | 0.498 (0.175) | 0.489 (0.182) | 0.570 (0.279) |
| | Week 52 (LOCF) | 0.748 (0.183) | 0.724 (0.180) | 0.765 (0.200) | 0.720 (0.150) | 0.689 (0.143) |
| | % Change | 63.1 (63.2) *** | 54.5 (62.1) *** | 67.7 (68.1) *** | 59.1 (44.2) *** | 39.9 (61.3) |
| Medium LDL-C | Baseline | 1.102 (0.830) | 1.134 (0.325) | 1.120 (0.337) | 1.030 (0.295) | 1.058 (0.382) |
| | Week 52 (LOCF) | 1.194 (0.300) | 1.244 (0.349) | 1.226 (0.307) | 1.127 (0.208) | 0.920 (0.248) |
| | % Change | 17.3 (49.9) *** | 15.5 (37.9) | 18.7 (53.7) *** | 18.9 (45.1) * | −2.8 (44.2) |
| Small LDL-C | Baseline | 0.682 (0.190) | 0.711 (0.236) | 0.690 (0.187) | 0.650 (0.160) | 0.643 (0.223) |
| | Week 52 (LOCF) | 0.517 (0.165) | 0.576 (0.223) | 0.522 (0.158) | 0.501 (0.139) | 0.381 (0.154) |
| | % Change | −20.6 (28.6) *** | −18.0 (21.3) *** | −20.6 (29.3) *** | −18.9 (28.2) *** | −38.6 (23.9) ** |
| Very small LDL-C | Baseline | 0.254 (0.080) | 0.262 (0.064) | 0.250 (0.080) | 0.264 (0.084) | 0.258 (0.113) |
| | Week 52 (LOCF) | 0.210 (0.061) | 0.233 (0.080) | 0.211 (0.056) | 0.207 (0.068) | 0.158 (0.056) |
| | % Change | −11.6 (30.2) *** | −10.3 (22.3) | −9.7 (30.1) *** | −15.8 (29.0) ** | −33.4 (21.4) ** |
| Very large HDL-C | Baseline | 0.046 (0.015) | 0.047 (0.016) | 0.046 (0.013) | 0.048 (0.016) | 0.038 (0.015) |
| | Week 52 (LOCF) | 0.048 (0.016) | 0.047 (0.018) | 0.048 (0.016) | 0.051 (0.017) | 0.044 (0.020) |
| | % Change | 4.4 (21.5) ** | 0.8 (18.3) | 4.1 (21.0) * | 5.9 (20.4) | 17.1 (36.1) |

TABLE 2-continued

Changes from baseline in the levels of cholesterol in CM, VLDL, LDL, and HDL subclasses measured by HPLC.

| | | | Bine eGFR Category | | | |
|---|---|---|---|---|---|---|
| Parameter | | All Participants | G1 | G2 | G3a-G3b | G4-G5 |
| (mmol/L) | n | 188 | 21 | 123 | 34 | 7 |
| Large HDL-C | Baseline | 0.130 (0.083) | 0.123 (0.103) | 0.130 (0.080) | 0.139 (0.082) | 0.096 (0.085) |
| | Week 52(LOCF) | 0.115 (0.088) | 0.107 (0.100) | 0.115 (0.088) | 0.124 (0.082) | 0.096 (0.090) |
| | % Change | −9.2 (45.1) ** | −14.1 (43.2) | −10.9 (44.7) ** | −4.9 (42.6) | 5.2 (53.4) |
| Medium HDL-C | Baseline | 0.374 (0.114) | 0.389 (0.131) | 0.382 (0.105) | 0.322 (0.118) | 0.216 (0.072) |
| | Week 52 (LOCF) | 0.443 (0.155) | 0.441 (0.155) | 0.448 (0.146) | 0.447 (0.170) | 0.336 (0.141) |
| | % Change | 19.3 (24.6) *** | 11.4 (21.3) * | 17.7 (23.9) *** | 20.6 (22.3) *** | 53.2 (25.3) ** |
| Small HDL-C | Baseline | 0.388 (0.076) | 0.414 (0.092) | 0.393 (0.070) | 0.382 (0.072) | 0.281 (0.057) |
| | Week 52 (LOCF) | 0.473 (0.087) | 0.482 (0.097) | 0.477 (0.079) | 0.467 (0.082) | 0.395 (0.106) |
| | % Change | 24.2 (23.3) *** | 18.1 (16.8) *** | 23.6 (23.3) *** | 24.6 (22.4) *** | 39.1 (20.9) ** |
| Very small HDL-C | Baseline | 0.148 (0.032) | 0.158 (0.032) | 0.146 (0.034) | 0.154 (0.023) | 0.128 (0.035) |
| | Week 52 (LOCF) | 0.181 (0.033) | 0.186 (0.035) | 0.181 (0.031) | 0.180 (0.024) | 0.155 (0.042) |
| | % Change | 27.9 (36.6) *** | 20.6 (25.0) ** | 30.9 (39.7) ** | 19.7 (22.8) *** | 23.5 (25.9) |

Observations:

The lowest eGFR group showed the greatest reduction in chylomicron (CM-C), very low-density lipoprotein (VLDL-C), small low-density lipoprotein cholesterol levels, and an increase in high-density lipoprotein cholesterol levels.

TABLE 3

Changes from baseline in the levels of safety parameters.

(A) With Statin

| | | Pemafibrate | | |
|---|---|---|---|---|
| | Placebo | 0.1 mg/day | 0.2 mg/day | 0.4 mg/day |
| Parameter | | | n | |
| | 178 | 45 | 382 | 72 |
| AE | | | | |
| Total | 73 (41.0) | 29 (64.4) | 164 (42.9) | 34 (47.2) |
| Serious | 2 (1.1) | 2 (4.4) | 6 (1.6) | 0 |
| Leading to withdrawal | 2 (1.1) | 2 (4.4) | 12 (3.1) | 0 |
| ADE | | | | |
| Total | 17 (9.6) | 3 (6.7) | 36 (9.4) | 2 (2.8) |
| Serious | 1 (0.6) | 0 | 2 (0.5) | 0 |
| Leading to withdrawal | 2 (1.1) | 1 (2.2) | 11 (2.9) | 0 |
| AST ≥ ULN × 3 | 0[1] | 0 | 1 (0.3) | 1 (1.4) |
| ALT ≥ ULN × 3 | 1 (0.6) | 1 (2.2) | 0 | 1 (1.4) |
| sCr ≥ ULN | 37 (20.8) | 8 (17.8) | 61 (16.0) | 11 (15.3) |
| CK ≥ 2.5 and < ULN × 5 | 4 (2.2) | 2 (4.4) | 7 (1.6) | 2 (2.8) |
| CK ≥ 5 and < ULN × 10 | 0 | 0 | 3 (0.6) | 0 |
| CK ≥ ULN × 10 | 0 | 0 | 1 (0.3) | 0 |

(B) Without Statin

| | | Pemafibrate | | |
|---|---|---|---|---|
| Parameter | Placebo | 0.1 mg/day | 0.2 mg/day | 0.4 mg/day |
| | | | n | |
| | 120 | 82 | 202 | 174 |
| AE | | | | |
| Total | 55 (45.8) | 27 (32.9) | 78 (38.6) | 60 (34.5) |
| Serious | 0 | 1 (1.2) | 4 (2.0) | 2 (1.1) |
| Leading to withdrawal | 0 | 2 (2.4) | 3 (1.5) | 6 (3.4) |

TABLE 3-continued

Changes from baseline in the levels of safety parameters.

| ADE | | | | |
|---|---|---|---|---|
| Total | 10 (8.3) | 3 (3.7) | 14 (6.9) | 16 (9.2) |
| Serious | 0 | 0 | 1 (0.5) | 1 (0.6) |
| Leading to withdrawal | 0 | 1 (1.2) | 2 (1.0) | 3 (1.7) |

| | n | | | |
|---|---|---|---|---|
| | 120 | 82 | 202 | 173 |
| AST ≥ ULN × 3 | 0 | 0 | 0 | 1 (0.6) |
| ALT ≥ ULN × 3 | 0 | 0 | 0 | 0 |
| sCr ≥ ULN | 16 (13.3) | 15 (18.3) | 34 (16.8) | 22 (12.7) |
| CK ≥ 2.5 and < ULN × 5 | 1 (0.8) | 2 (2.4) | 3 (1.5) | 0 |
| CK ≥ 5 and < ULN × 10 | 1 (0.8) | 0 | 0 | 1 (0.6) |
| CK ≥ ULN × 10 | 0 | 0 | 0 | 1 (0.6) |

Data are presented as the number of patients (percentage).
[1]n = 177.
AE, adverse event; ADR, adverse drug reaction, SAS, safety analysis set; AST aspartate aminotransferase; ULN, upper limit of normal; ALT, alanine aminotransferase; sCr, serum creatinine; CK, creatine kinase.

Observations:

The incidences of adverse events and adverse drug reactions were 82.0% and 31.7%, respectively, and these were not associated with baseline eGFR.

Example 4. Efficacy and Safety of Pemafibrate: Pooled Analysis of Phase 2 and 3 Studies in Dyslipidemic Patients with or without Statin Combination The present study analyzed data combined from 6 randomized double-blind placebo-controlled studies that were conducted in Japan and continued for 12 weeks unless otherwise noted: a phase 2 study in 224 patients with a history of documented dyslipidemia and plasma TG of 200 mg/dL (2.26 mmol/L) or higher, randomized to placebo, pemafibrate 0.05, 0.1, 0.2, 0.4 mg/day, or fenofibrate 100 mg/day; a phase 3 study in 526 patients with dyslipidemia, high TG levels, and low HDL-C levels, randomized to placebo, pemafibrate 0.1, 0.2, or 0.4 mg/day, or fenofibrate 100 or 200 mg/day; a study in 188 patients with dyslipidemia, randomized to pitavastatin in combination with pemafibrate 0.1, 0.2, or 0.4 mg/day; a 24-week study in 423 patients with dyslipidemia, randomized to pemafibrate 0.2 mg/day (fixed dose) or 0.2 [0.4] mg/day (conditional up-titration) with any statin; a 24-week phase 3 study in 166 patients with type 2 diabetes and hypertriglyceridemia, randomized to placebo or pemafibrate 0.2 or 0.4 mg/day; and a study in 27 patients with hypertriglyceridemia and insulin resistance, randomized to pemafibrate 0.4 mg/day or placebo. All studies were approved by the Institutional Review Board for each study institution and were conducted in accordance with the Declaration of Helsinki and under the guidelines of Good Clinical Practice.

In this study, we evaluated the efficacy and safety of pemafibrate at doses of 0.1 mg/day, 0.2 mg/day, and 0.4 mg/day, with and without statin. The primary efficacy endpoint was percent change in TG from baseline to 12 weeks. The secondary efficacy endpoints were also assessed from baseline to 12 weeks: percent change in HDL-C, LDL-C, non-HDL-C, TC, RemL-C, Apo AI, Apo AII, Apo B, Apo B48, Apo CII, Apo CIII, Apo CIII/Apo CII, and Apo E; percent change in HPLC findings for CM-C, VLDL-C, cholesterol content in 4 subclasses of LDL (large, medium, small, and very small LDLs), and cholesterol content for 5 subclasses of HDL (very large, large, medium, small, and very small HDLs); and changes in fibrinogen and FGF21. The primary safety endpoints were the incidence of adverse events and adverse drug reactions. Secondary safety endpoints were percentage of values above the upper limit of normal range for AST, ALT, sCr and CK, and change in sCr eGFR, CK, AST, ALT, gamma-glutamyl transferase (γ-GT), alkaline phosphatase (ALP), and total bilirubin.

Patients with renal dysfunction were defined as those with baseline eGFR<60 mL/min/1.73 m$^2$. Analysis was stratified by the presence or absence of renal dysfunction in the concomitant statin group, and efficacy and safety of pemafibrate were evaluated. In efficacy and safety evaluations excluding AEs, ADRs, and cutoff values for AST, ALT, sCr, and CK, findings were combined for pemafibrate subgroups receiving doses of 0.1 mg/day, 0.2 mg/day, and 0.4 mg/day.

For each lipid parameter, gel filtration HPLC was performed at Skylight Biotech, Inc. Other measurements were performed at LSI Medience Corporation. The FAS was used for analyzing efficacy parameters of effects on lipids, fibrinogen, and FGF21. The safety analysis set was used for safety parameters and included all patients who received at least one dose of the study drug. For lipid parameters, fibrinogen, and FGF21, LS means (95% confidence interval) were calculated at Week 12 (LOCF) using analysis of covariance (ANCOVA) with baseline values as the co-variable within each category. For safety parameters, LS means (95% confidence interval) were calculated at Week 12 using ANCOVA with baseline values as the co-variable within each category. SAS version 9.2 was used for analyses.

The results for small LDL-C, very small LDL-C, small HDL-C, and very small HDL-C, for based on eGFR are presented in Table 4. As can be seen, improvements in small and very small LDL-C and HDL particle sizes are seen in the lower eGFR group.

TABLE 4

Changes in lipoproteins from baseline to week 12 (with statin) (FAS).

| Parameter | | Baseline eGFR ≥ 60 mL/min/1.73 m² | | Baseline eGFR < 60 mL/min/1.73 m² | |
|---|---|---|---|---|---|
| | | Placebo n 141 | Pemafibrate 0.1-0.4 mg/day 428 | Placebo n 33 | Pemafibrate 0.1-0.4 mg/day 58 |
| Small LDL-C (mmol/L) | Baseline | 0.641 (0.191) | 0.644 (0.182) | 0.643 (0.147) | 0.644 (0.189) |
| | Week 12 (LOCF) | 0.618 (0.177) | 0.576 (0.170) | 0.640 (0.154) | 0.577 (0.203) |
| | % Change | −1.8 (−6.1, 2.5) | −6.0 (−8.5, −3.5) | 1.5 (−6.7, 9.7) | −7.8 (−14.0, −1.7) |
| Very small LDL-C (mmol/L) | Baseline | 0.269 (0.082) | 0.275 (0.081) | 0.272 (0.083) | 0.274 (0.081) |
| | Week 12 (LOCF) | 0.258 (0.072) | 0.231 (0.070) | 0.272 (0.094) | 0.229 (0.084) |
| | % Change | −2.2 (−5.9, 1.6) | −12.5 (−14.7, −10.4) *** | 1.4 (−6.2, 8.9) | −14.6 (−20.3, −8.9) ** |
| Small HDL-C (mmol/L) | Baseline | 0.380 (0.079) | 0.376 (0.073) | 0.363 (0.066) | 0.365 (0.065) |
| | Week 12 (LOCF) | 0.380 (0.078) | 0.470 (0.083) | 0.365 (0.061) | 0.484 (0.080) |
| | % Change | 1.3 (−1.5, 4.1) | 26.7 (25.1, 28.3) *** | 1.3 (−5.0, 7.5) | 34.9 (30.1, 39.6) *** |
| Very small HDL-C (mmol/L) | Baseline | 0.171 (0.035) | 0.174 (0.034) | 0.170 (0.043) | 0.170 (0.036) |
| | Week 12 (LOCF) | 0.172 (0.036) | 0.204 (0.038) | 0.172 (0.042) | 0.208 (0.037) |
| | % Change | 1.1 (−1.9, 4.1) | 19.4 (17.7, 21.1) *** | 2.5 (−3.9, 8.9) | 25.2 (20.4, 30.0) *** |

REFERENCES CITED

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

1 Miller M, Stone N J, Ballantyne C, et al. American Heart Association Clinical Lipidology, Thrombosis, and Prevention Committee of the Council on Nutrition, Physical Activity, and Metabolism; Council on Arteriosclerosis, Thrombosis and Vascular Biology; Council on Cardiovascular Nursing; Council on the Kidney in Cardiovascular Disease. Triglycerides and cardiovascular disease: a scientific statement from the American Heart Association. Circulation. 2011; 123(20):2292-2333.
2 Scherer J, Singh V P, Pitchumoni C S, Yadav D. Issues in hypertriglyceridemic pancreatitis: an update. J Clin Gastroenterol. 2014; 48(3):195-203.
3 Anderson F, Thomson S R, Clarke D L, Buccimazza I. Dyslipidaemic pancreatitis clinical assessment and analysis of disease severity and outcomes. Pancreatology. 2009; 9(3):252-257.
4 Deng L H, Xue P, Xia Q, Yang N X, Wan M H. Effect of admission hypertriglyceridemia on the episodes of severe acute pancreatitis. World J Gastroenterol. 2008; 14(28): 4558-4561. Staels B, Dallongeville J, Auwerx J, Schoonjans K, Leitersdorf E, Fruchart J C. Mechanism of action of fibrates on lipid and lipoprotein metabolism. Circulation. 1998; 98:2088-2093.
6 National Institutes of Health, National Heart, Lung, and Blood Institute. Third Report of the National Cholesterol Education Program (NCEP) Expert Panel on Detection, Evaluation, and Treatment of High Blood Cholesterol in Adults (Adult Treatment Panel III) Final Report. 2002; pII-1-61; September 2002.
7 Pirillo A, Catapano A L. Update on the management of severe hypertriglyceridemia—focus on free fatty acid forms of omega-3. Drug Des Devel Ther. 2015; 9:2128-2137.
8 Task Force for the management of dyslipidaemias of the European Society of Cardiology (ESC) and the European Atherosclerosis Society (EAS). ESC/EAS Guidelines for the management of dyslipidaemias. Eur Heart J. 2011; 32:1769-1818.
9 Package insert for Lipidil® Tablets, revised May 2012 (2nd edition).
10 Package insert for Bezatol® SR Tablets, revised June 2009 (12th edition).
11 Package insert for Clofibrate Capsules, revised July 2009 (6th edition).
12 Ciprofibrate 100 mg tablets, Summary of Product Characteristics at eMedicines Compendium.
13 Lopid 300 mg capsules and 600 mg tablets, Summary of Product Characteristics at eMedicines Compendium.
14 Package ins ert for Tricor® tablets, revised September 2011.
15 Package insert for Trilipix® capsule, revised September 2012.
16 Package insert for Lopid® tablets, revised September 2010.

The invention claimed is:
1. A method of treating atherogenic dyslipidemia in a renally impaired dyslipidemic patient having an estimated glomerular filtration rate (eGFR) of less than 60 mL/min/ 1.73 m² comprising administering to the patient 0.4 mg/day of pemafibrate or a pharmaceutically acceptable salt thereof in combination with moderate to high intensity statin therapy.
2. The method of claim 1, wherein the patient has an eGFR of less than 45 mL/min/1.73 m².
3. The method of claim 1, wherein the patient has an eGFR of less than 30 mL/min/1.73 m².
4. The method of claim 1, wherein the patient has end stage renal disease.
5. The method of claim 1, wherein the patient has chronic kidney disease.
6. The method of claim 1, wherein said patient is characterized by increased TG-rich lipoproteins and decreased HDL-C levels.
7. The method of claim 1, wherein said patient has a TG concentration greater than 150 mg/dL and an HDL-C concentration less than 40 mg/dL.

8. The method of claim 1, wherein the 0.4 mg per day is the same amount as administered to a non-renally impaired patient.

9. A method of treating atherogenic dyslipidemia in a renally impaired dyslipidemic patient having an estimated glomerular filtration rate (eGFR) of less than 60 mL/min/1.73 m$^2$ comprising administering to the patient about 0.4 mg/day of pemafibrate or a pharmaceutically acceptable salt thereof.

10. The method of claim 9, wherein the 0.4 mg/day of pemafibrate or pharmaceutically acceptable salt thereof is administered in two equal doses of about 0.2 mg.

11. The method of claim 9, wherein the patient has an eGFR of less than 45 mL/min/1.73 m$^2$.

12. The method of claim 9, wherein the patient has an eGFR of less than 30 mL/min/1.73 m$^2$.

13. The method of claim 9, wherein the patient has end stage renal disease.

14. The method of claim 9, wherein the patient has chronic kidney disease.

15. The method of claim 9, wherein the patient has a TG concentration greater than 150 mg/dL and an HDL-C concentration less than 40 mg/dL.

\* \* \* \* \*